United States Patent
Shaw et al.

(10) Patent No.: US 9,241,988 B2
(45) Date of Patent: Jan. 26, 2016

(54) DISACCHARIDE SYNTHETIC LIPID COMPOUNDS AND USES THEREOF

(71) Applicants: AVANTI POLAR LIPIDS, INC., Alabaster, AL (US); AC IMMUNE SA, Lausanne (CH)

(72) Inventors: Walter A Shaw, Birmingham, AL (US); Stephen W Burgess, Chelsea, AL (US); Shengrong Li, Birmingham, AL (US); David T Hickman, Saint-Sulpice (CH); Maria Pilar Lopez-Deber, Lausanne (CH)

(73) Assignees: AVANTI POLAR LIPIDS, INC., Alabaster, AL (US); AC IMMUNE SA, Lausanne (CH)

( * ) Notice: Subject to any disclaimer, the term of this patent is extended or adjusted under 35 U.S.C. 154(b) by 20 days.

(21) Appl. No.: 13/842,424

(22) Filed: Mar. 15, 2013

(65) Prior Publication Data

US 2013/0273149 A1    Oct. 17, 2013

Related U.S. Application Data

(60) Provisional application No. 61/623,393, filed on Apr. 12, 2012.

(51) Int. Cl.
    *C07H 13/06* (2006.01)
    *A61K 39/39* (2006.01)
    *A61K 39/00* (2006.01)

(52) U.S. Cl.
    CPC ............. *A61K 39/39* (2013.01); *A61K 39/0007* (2013.01); *C07H 13/06* (2013.01); *A61K 2039/55572* (2013.01)

(58) Field of Classification Search
    None
    See application file for complete search history.

(56) References Cited

U.S. PATENT DOCUMENTS

| 5,066,794 A | 11/1991 | Shiba |
| 5,654,289 A | 8/1997 | Kodama et al. |
| 6,005,099 A * | 12/1999 | Davies et al. ............... 536/55.2 |
| 7,491,707 B1 | 2/2009 | Jiang et al. |
| 2010/0221269 A1 | 9/2010 | Boons |

FOREIGN PATENT DOCUMENTS

JP    01-221387    9/1989

OTHER PUBLICATIONS

Wolff, Manfred E. "Burger's Medicinal Chemistry, 5ed, Part I", John Wiley & Sons, 1995, pp. 975-977.*
Banker, G.S. et al, "Modern Pharmaceutics, 3ed.", Marcel Dekker, New York, 1996, pp. 451.*
Kawasaki et al., Journal of Endotoxin Research, 2005, 11(1), pp. 57-61.*
Dunn-Siegrist, et al. "Toll-like receptor activation of human cells by synthetic triacylated lipid A-like molecules" The Journal of Biological Chemistry Mar. 20, 2012; jbc.M112.348383; pp. 1-20.

* cited by examiner

*Primary Examiner* — Traviss C McIntosh, III
(74) *Attorney, Agent, or Firm* — Thomas G. Peterson; Bradley Arant Boult Cummings LLP

(57) ABSTRACT

Essentially pure compounds of the formulas (I) to (XX) are provided. Compositions and methods for enhancing or stimulating an immune response are also provided. The compounds, provided are advantageous in that the compounds are essentially pure and free from contaminants encountered when such compounds are purified from natural sources.

12 Claims, 6 Drawing Sheets

DISACCHARIDE SYNTHETIC LIPID COMPOUNDS AND USES THEREOF

This application claims the benefit of U.S. Provisional Application No. 61/623,393 filed Apr. 12, 2012.

FIELD OF THE DISCLOSURE

The present disclosure relates generally to compounds for use in enhancing or stimulating an immune response. More specifically, the present disclosure relates to synthetic disaccharide lipid A analogues having the structure of formulas (I)-(XX), or pharmaceutically acceptable salts thereof. The use of such compounds for inducing and stimulating an immune response, pharmaceutical compositions containing such compounds and vaccine compositions comprising such compounds are also disclosed.

BACKGROUND

It is known that endotoxin which is an outer membrane component of various Gram negative bacilli has various biological activities, such as enhancement of immune function. The main active portion of the endotoxin resides in a disaccharide moiety referred to as lipid A. Various lipid A derivatives have been studied and reported to have biological activities similar to natural lipid A. However, many such compounds are purified from natural sources which can lead to problems with consistency and purity of these compounds. Much research has centered on providing pure or essentially pure forms of such compounds.

DETAILED DESCRIPTION

Definitions

Figure 1A:
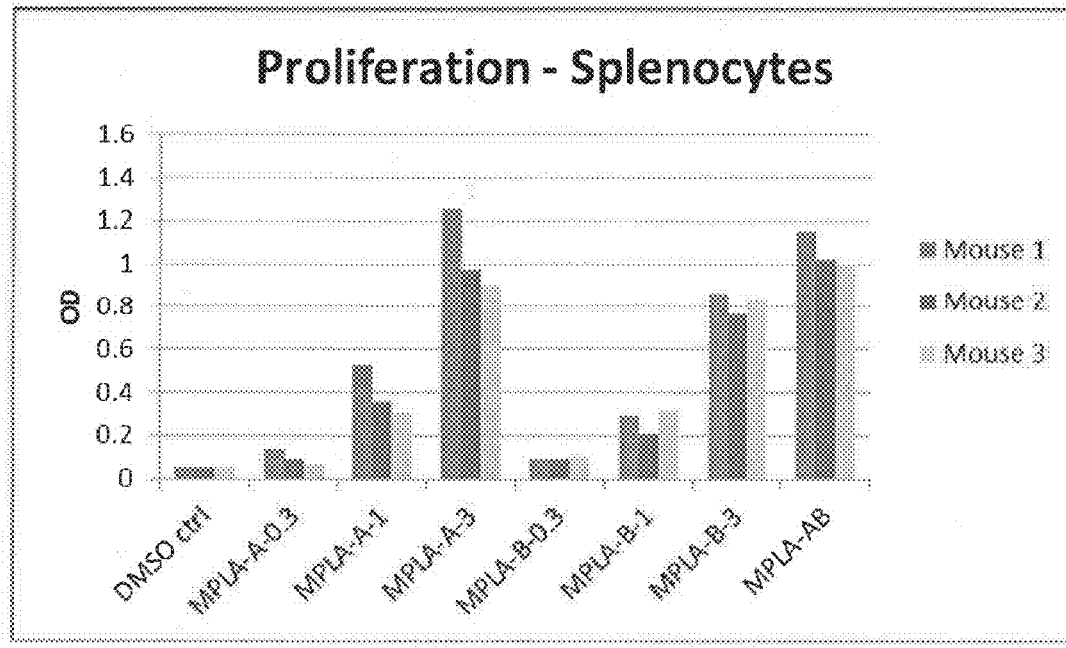
FIG. 1A shows the effect of the synthetic disaccharide lipid compounds of the present disclosure on proliferation of splenocytes in vitro.

As used herein, the terms "prevention", "prevent", "preventing", "suppression", "suppress" and "suppressing" as used herein refer to a course of action (such as administering a compound or pharmaceutical composition) initiated prior to the onset of a symptom, aspect, or characteristics of a disease or condition so as to prevent or reduce such symptom, aspect, or characteristics. Such preventing and suppressing need not be absolute to be useful.

As used herein, the terms "treatment", "treat" and "treating" as used herein refers a course of action (such as administering a compound or pharmaceutical composition) initiated after the onset of a symptom, aspect, or characteristics of a disease or condition so as to eliminate or reduce such symptom, aspect, or characteristics. Such treating need not be absolute to be useful.

As used herein, the term "in need of treatment" as used herein refers to a judgment made by a caregiver that a patient requires or will benefit from treatment. This judgment is made based on a variety of factors that are in the realm of a caregiver's expertise, but that includes the knowledge that the patient is ill, or will be ill, as the result of a disease or condition that is treatable by a method or compound of the disclosure.

As used herein, the term "in need of prevention" as used herein refers to a judgment made by a caregiver that a patient requires or will benefit from prevention. This judgment is made based on a variety of factors that are in the realm of a caregiver's expertise, but that includes the knowledge that the patient will be ill or may become ill, as the result of a disease or condition that is preventable by a method or compound of the disclosure.

As used herein, the terms "individual", "subject" or "patient" as used herein refers to any animal, including mammals, such as mice, rats, other rodents, rabbits, dogs, cats, swine, cattle, sheep, horses, or primates, and humans. The term may specify male or female or both, or exclude male or female.

As used herein, the term "therapeutically effective amount" as used herein refers to an amount of a compound, either alone or as a part of a pharmaceutical composition, that is capable of having any detectable, positive effect on any symptom, aspect, or characteristics of a disease or condition. Such effect need not be absolute to be beneficial.

As used herein, the term "alkyl", whether used alone or as part of a substituent or linking group, includes straight hydrocarbon groups comprising from one to twenty carbon atoms. Thus the phrase includes straight chain alkyl groups such as methyl, ethyl, propyl, butyl, pentyl, hexyl, heptyl, octyl, nonyl, decyl, undecyl, dodecyl and the like. The phrase also includes branched chain isomers of straight chain alkyl groups, including but not limited to, the following which are provided by way of example: —CH(CH$_3$)$_2$, —CH(CH$_3$)(CH$_2$CH$_3$), —CH(CH$_2$CH$_3$)$_2$, —C(CH$_3$), —C(CH$_2$CH$_3$)$_3$, —CH$_2$CH(CH$_3$)$_2$, —CH$_2$CH(CH$_3$)(CH$_2$CH$_3$), —CH$_2$CH(CH$_2$CH$_3$)$_2$, —CHC(CH$_3$)$_3$, —CH$_2$C(CH$_2$CH$_3$)$_3$, —CH(CH$_3$)CH(CH$_3$)(CH$_2$CH$_3$), —CH$_2$CH$_2$CH(CH$_3$)$_2$, —CH$_2$CH$_2$CH(CH$_3$)(CH$_2$CH$_3$)—, CH$_2$CH$_2$CH(CH$_2$CH$_3$)$_2$, —CH$_2$CH$_2$C(CH$_3$)$_3$, —CH$_2$CH$_2$C(CH$_2$CH$_3$)$_3$, —CH(CH$_3$)CH$_2$CH(CH$_3$)$_2$, —CH(CH$_3$)CH(CH$_3$)CH(CH$_3$)CH(CH$_3$)$_2$, —CH(CH$_2$CH$_3$)CH(CH$_3$)CH(CH$_3$)(CH$_2$CH$_3$) and others. The phrase also includes cyclic alkyl groups such as cyclopropyl, cyclobutyl, cyclopentyl, cyclohexyl, cycloheptyl, and cyclooctyl and such rings substituted with straight and branched chain alkyl groups as defined above. The phrase also includes polycyclic alkyl groups such as, but not limited to, adamantyl norbornyl, and bicyclo[2.2.2]octyl and such rings substituted with straight and branched chain alkyl groups as defined above.

As used herein, the term "alkylene", whether used alone or as part of a substituent group, includes any group obtained by removing a hydrogen atom from an alkyl group; an alkylene group forms two bonds with other groups.

As used herein, the term "alkenyl", whether used alone or as part of a substituent group, includes an alkyl group having at least one double bond between any two adjacent carbon atoms.

As used herein, the term "unsubstituted alkyl" and "unsubstituted alkenyl" refers to alkyl and alkenyl groups that do not contain heteroatoms.

The phrase "substituted alkyl" and "substituted alkenyl" refers to alkyl and alkenyl groups as defined above in which one or more bonds to a carbon(s) or hydrogen(s) are replaced by a bond to non-hydrogen or non-carbon atoms such as, but not limited to, a halogen atom in halides such as F, Cl, Br, and I; and oxygen atom in groups such as carbonyl, carboxyl, hydroxyl groups, alkoxy groups, aryloxy groups, and ester groups; a sulfur atom in groups such as thiol groups, alkyl and aryl sulfide groups, sulfone groups, sulfonyl groups, and sulfoxide groups; a nitrogen atom in groups such as amines, amides, alkylamines, dialkylamines, arylamines, alkylarylamines, diarylamines, N-oxides, imides, enamines imines, oximes, hydrazones, and nitriles; a silicon atom in groups such as in trialkylsilyl groups, dialkylarylsilyl groups, alkyldiarylsilyl groups, and triarylsilyl groups; and other heteroatoms in various other groups. Other alkyl groups include those in which one or more bonds to a carbon or hydrogen atom is replaced by a bond to an oxygen atom such that the substituted alkyl group contains a hydroxyl, alkoxy, aryloxy group, or heterocyclyloxy group. Still other alkyl groups include alkyl groups that have an amine, alkylamine, dialkylamine, arylamine, (alkyl)(aryl)amine, diarylamine, heterocyclylamine, (alkyl)(heterocyclyl)-amine, (aryl)(heterocyclyl)amine, or diheterocyclylamine group.

Disaccharide Synthetic Lipid Compounds

The present disclosure provides synthetic disaccharide lipid compounds of the general structures I to XX below. The disclosed synthetic disaccharide lipid compounds are 3-0-deacyl disaccharide compounds containing from 3 to 5 acyl groups at the positions disclosed herein. In a particular embodiment, the compounds are mono-phosphoryl. Such compounds are useful as immunostimulants for inducing and stimulating an immune response and are useful as adjuvants in immunogenic compositions such as, but not limited to, vaccines.

The compounds of the present disclosure are chemically synthesized and are therefore provided in essentially pure form. By "essentially pure", it is meant that the synthetic disaccharide lipid compounds are at least 80%, at least 85%, at least 90%, at least 95%, at least 96%, at least 97%, at least 98% or at least 99% pure with respect to the synthetic disaccharide lipid compounds (measured on a weight basis). In a particular aspect, the synthetic disaccharide lipid compounds are at least 95% pure (measured on a weight basis). In another aspect, the synthetic disaccharide lipid compounds are at least 96% pure (measured on a weight basis). In another aspect, the synthetic disaccharide lipid compounds are at least 97% pure (measured on a weight basis). In another aspect, the synthetic disaccharide lipid compounds are at least 98% pure (measured on a weight basis). In another aspect, the synthetic disaccharide lipid compounds are at least 99% pure (measured on a weight basis).

This level of purity allows the synthetic disaccharide lipid compounds of the present disclosure to be used in various pharmacologic applications for which naturally purified lipid A compounds are unsuitable. For instance, naturally purified lipid A compounds are co-purified with various amounts of proteins, nucleic acids, other lipids and other products from the bacterial cells from which they are purified. In addition, the levels of such impurities vary from purification to purification. Furthermore, the naturally purified lipid A compounds are often present in various forms. For instance, the number of acyl chains present on the disaccharide backbone may vary in a given preparation, as well as the length of a given acyl chain at a particular position. Therefore, the compounds of the present disclosure are essentially free of contaminants found in compounds purified from natural sources, such as, but not limited to, proteins, nucleic acids, other lipids and other products from a bacterial cell. In addition, the compounds of the present disclosure are essentially free of contaminants generated during chemical synthesis. As such, the compounds of the present disclosure provide an advantage over the compounds known in the art.

As used herein, the term "essentially free" means that the compounds of the present disclosure contain less than 1%, less than 2%, less than 3%, less than 4%, less than 5%, less than 10%, less than 15% or less than 20% of such contaminants as determined with respect to the synthetic disaccharide lipid compound (as measured on a weight basis). Relevant contaminants include, but are not limited to, related compounds having different number and/or length of the acyl chains, those contaminants encountered during isolation of corresponding compounds from natural sources and contaminants encountered as a result of chemical synthesis. In one aspect, the synthetic disaccharide lipid compounds contain less than 1% of such contaminants as determined with respect to the synthetic disaccharide lipid compound (as measured on a weight basis). In one aspect, the synthetic disaccharide lipid compounds contain less than 2% of such contaminants as determined with respect to the synthetic disaccharide lipid compound (as measured on a weight basis). In one aspect, the synthetic disaccharide lipid compounds contain less than 3% of such contaminants as determined with respect to the synthetic disaccharide lipid compound (as measured on a weight basis). In one aspect, the synthetic disaccharide lipid compounds contain less than 4% of such contaminants as determined with respect to the synthetic disaccharide lipid compound (as measured on a weight basis). In one aspect, the synthetic disaccharide lipid compounds contain less than 5% of such contaminants as determined with respect to the synthetic disaccharide lipid compound (as measured on a weight basis).

The foregoing concerns result in the properties of the naturally purified lipid A compounds being variable from preparation to preparation. Furthermore, individual subject reaction to such naturally occurring lipid A compounds may vary as well. The provision of the compounds of the present disclosure in an essentially pure form reduces the foregoing concerns and allows the use of compounds of the present disclosure in applications in which naturally occurring lipid A compositions are unsuited.

The art is also aware of various mono-phosphorylated hexaacyl disaccharide compounds. For example, such compounds are provided under the name PHAD (or PHAD™) and are available from Avanti Polar Lipids (Alabaster, Ala.).

However, these compounds have an acyl group at the 3 position.

3-O-deacyl mono-phosphorylated pentaacyl disaccharide compounds are known in the art. However, such 3-O-deacyl mono-phosphorylated pentaacyl disaccharide compounds have been purified from natural sources and treated chemically to remove the acyl chain present at the 3 position. As a result, the variability in the composition of the prior art 3-O-deacyl mono-phosphorylated pentaacyl disaccharide compounds is relevant. In addition, the foregoing, chemical modification procedure also introduces additional variability.

Therefore, the prior art has not provided 3-O-deacyl mono-phosphorylated disaccharide compounds in an essentially pure form and/or essentially free from contaminants. The present disclosure provides synthetic disaccharide lipid compounds containing from 3 to 5 acyl chains, wherein the 3-5 acyl chains are positioned at the 2', 3' and 2 positions of non-reducing and reducing sugars, respectively. A representative disaccharide compound with the 2', 3', 2 and 3 positions is shown below.

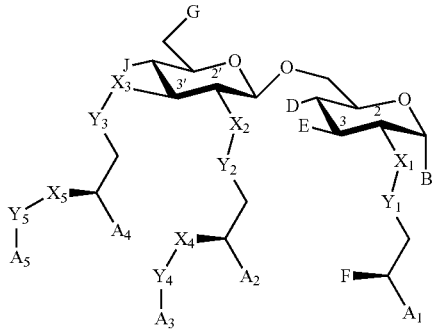

For clarity, an acyl chain is not required to be present at each of the positions 2', 3' or 2, provided that the synthetic disaccharide lipid compounds has a total of 3-5 acyl chains at the recited positions (2', 3' and 2). Furthermore, a recited position may contain more than 1 acyl chain, while another recited position may not be associated with an acyl chain, provided that the synthetic disaccharide lipid compounds has a total of 3-5 acyl chains at the recited positions (2', 3' and 2).

For example, an exemplary synthetic disaccharide lipid compounds of the present disclosure may contain 2 acyl chains at the 3' position, 2 acyl chains at the 2 position and 1 acyl chain at the 2' position (for a total of 5 acyl chains). Furthermore, an exemplary synthetic disaccharide lipid compounds of the present disclosure may contain 2 acyl chains at the 3' position, 1 acyl chain at the 2 position and 1 acyl chain at the 2' position (for a total of 4 acyl chains). Still further, an exemplary synthetic disaccharide lipid compounds of the present disclosure may contain 1 acyl chain at the 3' position, 2 acyl chain at the 2 position and 1 acyl chain at the 2' position (for a total of 4 acyl chains). Still further, an exemplary synthetic disaccharide lipid compounds of the present disclosure may contain no acyl chains at the 3' position, 2 acyl chain at the 2 position and 1 acyl chain at the 2' position (for a total of 3 acyl chains).

The synthetic disaccharide lipid compounds of the present disclosure contain from 3 to 5 acyl chains. In one embodiment, the length of the acyl chains may vary from 6 to 19 carbons in length. For clarity, the length of the 3 to 5 acyl chains present in the 3 synthetic disaccharide lipid compounds may each be the same or may be different. In a particular embodiment, the length of the 3 to 5 acyl chains is the same. The 3 to 5 acyl chains may be saturated and contain no double bonds or the 3 to 5 acyl chains may be unsaturated. When such acyl chains are unsaturated, each unsaturated acyl chain may contain from 1 to 3 double bonds. In one embodiment, the 3 to 5 acyl chains are all saturated. In another embodiment, at least one of the 3 to 5 acyl chains is unsaturated and contains a single double bond and the remainder of the acyl chains are saturated.

In one embodiment, such synthetic disaccharide lipid compounds have the general structure shown in formula I:

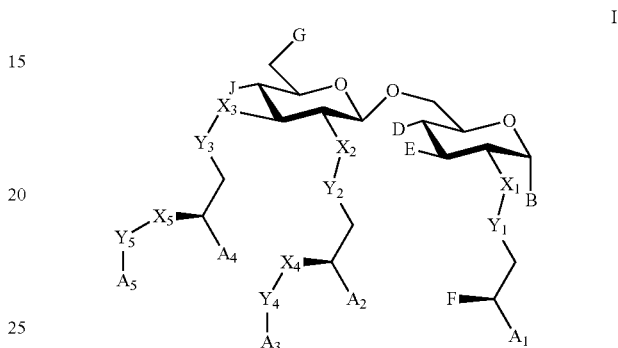

or a pharmaceutically acceptable salt or prodrug thereof, wherein:

$X_1$, $X_2$, $X_3$, $X_4$ and $X_5$ are each independently absent or selected from $C_1$-$C_8$ alkyl, —O—, —NH— or —CH$_2$—;

$Y_1$, $Y_2$, $Y_3$, $Y_4$ and $Y_5$ are each independently selected from H, $C_1$-$C_4$ alkyl, —CH$_2$—, or —C(=O)—, provided that at least 3 of $Y_1$, $Y_2$, $Y_3$, $Y_4$ and $Y_5$ are a group other than H and further provided that when one of $Y_1$, $Y_2$, $Y_3$, $Y_4$ and $Y_5$ is H, then the groups which are linked, directly or indirectly, to the $Y_1$, $Y_2$, $Y_3$, $Y_4$ or $Y_5$ are absent;

D, E, G and F are each independently selected from $C_1$-$C_4$ alkyl, —OH, —SH, —OC(=O)(CH$_2$)$_m$—CH$_3$, —OC(=O)(CH$_2$)$_n$C(=O)OH or —OC(=O)CH(NH$_2$)(CH$_2$)$_n$C(=O)OH;

J and B are each independently selected from OH, OR$_1$, H, —OP(=O)(OH)$_2$—, OP(=O)(OR$_2$)$_2$—, —OS(=O)(OH)$_2$—, —OS(=O)(OR$_2$)$_2$—, —OS(OH)$_2$—, —OS(OR$_2$)$_2$—, —C(=O)OH—, —C(=O)OR$_2$— or an acidic group;

$A_1$, $A_2$, and $A_4$ are each independently selected from $C_6$ to $C_{18}$ substituted or unsubstituted alkyl or alkenyl;

$A_3$ and $A_5$ are each independently selected from $C_7$ to $C_{19}$ substituted or unsubstituted alkyl or alkenyl;

$R_1$ is a substituted or unsubstituted $C_1$-$C_4$ alkyl;

$R_2$ is independently for each occurrence, H, alkyl, substituted alkyl or N-linked amino acid residue; and m and n are each independently an integer from 0 to 5.

In first aspect of this embodiment, at least one of $X_3$, $X_4$ and $X_5$ are —O—, at least two of $X_3$, $X_4$ and $X_5$ are —O—, or all three of $X_3$, $X_4$ and $X_5$ are —O—.

In a second aspect of this embodiment, at least one of $X_1$ and $X_2$ are —NH—, or both of $X_1$ and $X_2$ are —NH—.

In a third aspect of this embodiment, $X_3$, $X_4$ and $X_5$ are —O— and $X_1$ and $X_2$ are —NH—.

In a fourth another aspect of this embodiment, $X_1$ to $X_5$ are as defined in the first through third aspects and at least one of $Y_1$, $Y_2$, $Y_3$, $Y_4$ and $Y_5$ are —C(=O)—, at least two of $Y_1$, $Y_2$, $Y_3$, $Y_4$ and $Y_5$ are —C(=O)—, at least three of $Y_1$, $Y_2$, $Y_3$, $Y_4$ and $Y_5$ are —C(=O)—, at least four of $Y_1$, $Y_2$, $Y_3$, $Y_4$ and $Y_5$ are —C(=O)—, or all of $Y_1$, $Y_2$, $Y_3$, $Y_4$ and $Y_5$ are —C(=O)—.

In a fifth aspect of this embodiment, $X_3$, $X_4$ and $X_5$ are —O— and $X_1$ and $X_2$ are —NH— and all of $Y_1$, $Y_2$, $Y_3$, $Y_4$ and $Y_5$ are —C(=O)—.

In a sixth aspect of this embodiment, $X_1$ to $X_5$ are as defined in the first through fifth aspects, $Y_1$ to $Y_5$ are as defined in the fourth and fifth aspects and J is —OP(=O)(OH)$_2$— and B is —OH.

In any of the first through sixth aspects of this embodiment, D, E, F and G are each OH.

In any of the first through sixth aspects of this embodiment, $A_1$ $A_2$, and $A_4$ are each independently $C_9$ to $C_{13}$ unsubstituted alkyl and $A_3$ and $A_5$ are each independently are $C_{11}$ to $C_{15}$ unsubstituted alkyl.

In any of the first through sixth aspects of this embodiment, $A_1$ $A_2$, and $A_4$ are each $C_{11}$ unsubstituted alkyl and $A_3$ and $A_5$ are each $C_{13}$ unsubstituted alkyl.

In any of the first through sixth aspects of this embodiment, $A_1$ $A_2$, and $A_4$ are each $C_{11}$ unsubstituted alkyl, $A_3$ is a $C_{11}$ unsubstituted alkyl and $A_5$ is a $C_{13}$ unsubstituted alkyl.

In another embodiment, such synthetic disaccharide lipid compounds have the general structure shown in formula II:

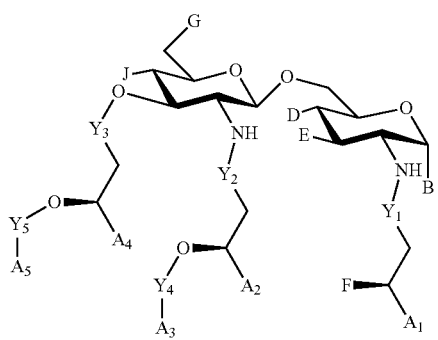

II or a pharmaceutically acceptable salt or prodrug thereof, wherein:

$Y_1$, $Y_2$, $Y_3$, $Y_4$ and $Y_5$ are each independently selected from —CH$_2$— or —C(=O)—, provided that at least 3 of $Y_1$, $Y_2$, $Y_3$, $Y_4$ and $Y_5$ are a group other than H and further provided that when one of $Y_1$, $Y_2$, $Y_3$, $Y_4$ and $Y_5$ is H, then the groups which are linked, directly or indirectly, to the $Y_1$, $Y_2$, $Y_3$, $Y_4$ or $Y_5$ are absent;

D, E, G and F are each independently selected from —OH, —SH, —OC(=O)(CH$_2$)$_m$—CH$_3$, OC(=O)(CH$_2$)$_n$C(=O)OH or —OC(=O)CH(NH$_2$)(CH$_2$)$_n$C(=O)OH;

J and B are each independently selected from OH, OR$_1$, H, —OP(=O)(OH)$_2$—, OP(=O)(OR$_2$)$_2$—, —OS(=O)(OH)$_2$—, —OS(=O)(OR$_2$)$_2$—, —OS(OH)$_2$—, —OS(OR$_2$)$_2$—, —C(=O)OH—, —C(=O)OR$_2$— or an acidic group;

$A_1$, $A_2$, and $A_4$ are each independently selected from $C_6$ to $C_{18}$ substituted or unsubstituted alkyl or alkenyl;

$A_3$ and $A_5$ are each independently selected from $C_7$ to $C_{19}$ substituted or unsubstituted alkyl or alkenyl;

$R_1$ is a substituted or unsubstituted $C_1$-$C_4$ alkyl;

$R_2$ is independently for each occurrence, H, alkyl, substituted alkyl or N-linked amino acid residue; and m and n are each independently an integer from 0 to 5.

In a first aspect of this embodiment, at least one of $Y_1$, $Y_2$, $Y_3$, $Y_4$ and $Y_5$ are —C(=O)—, at least two of $Y_1$, $Y_2$, $Y_3$, $Y_4$ and $Y_5$ are —C(=O)—, at least three of $Y_1$, $Y_2$, $Y_3$, $Y_4$ and $Y_5$ are —C(=O), at least four of $Y_1$, $Y_2$, $Y_3$, $Y_4$ and $Y_5$ are —C(=O)— or all of $Y_1$, $Y_2$, $Y_3$, $Y_4$ and $Y_5$ are —C(=O)—.

In a second aspect of this embodiment, $Y_1$, $Y_2$, $Y_3$, $Y_4$ and $Y_5$ are as defined in the first aspect and J is —OP(=O)(OH)$_2$— and B is —OH.

In any of the first through second aspects of this embodiment, D, E, F and G are each OH.

In any of the first through second aspects of this embodiment, $A_1$, $A_2$, and $A_4$ are each independently a $C_9$ to $C_{13}$ unsubstituted alkyl and $A_3$ and $A_5$ are each independently a $C_{11}$ to $C_{15}$ unsubstituted alkyl.

In any of the first through second aspects of this embodiment, $A_1$, $A_2$, and $A_4$ are each $C_{11}$ unsubstituted alkyl and $A_3$ and $A_5$ are each $C_{13}$ unsubstituted alkyl.

In any of the first through second aspects of this embodiment, $A_1$, $A_2$, and $A_4$ are each $C_{11}$ unsubstituted alkyl, $A_3$ is $C_{11}$ unsubstituted alkyl and $A_5$ is a $C_{13}$ unsubstituted alkyl.

In still another embodiment, synthetic disaccharide lipid compounds have the general structure shown in formula III:

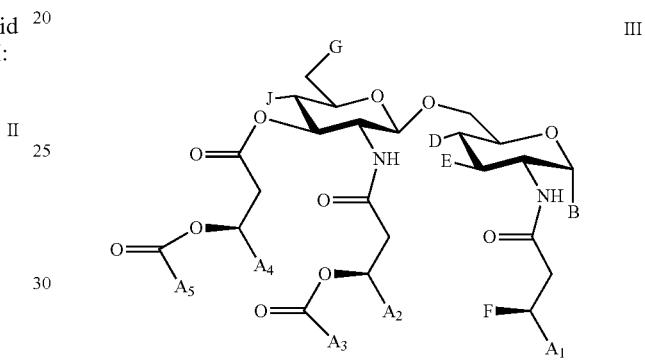

III or a pharmaceutically acceptable salt or prodrug thereof, wherein:

D, E, G and F are each independently selected from —OH, —SH, —OC(=O)(CH$_2$)$_m$—CH$_3$, OC(=O)(CH$_2$)$_n$C(=O)OH or —OC(=O)CH(NH$_2$)(CH$_2$)$_n$C(=O)OH;

J and B are each independently selected from OH, OR$_1$, H, —OP(=O)(OH)$_2$—, OP(=O)(OR$_2$)$_2$—, OS(=O)(OH)$_2$—, —OS(=O)(OR$_2$)$_2$—, —OS(OH)$_2$—, —OS(OR$_2$)$_2$—, —C(=O)OH—, —C(=O)OR$_2$— or an acidic group;

$A_1$, $A_2$, and $A_4$ are each independently selected from $C_6$ to $C_{18}$ substituted or unsubstituted alkyl or alkenyl;

$A_3$ and $A_5$ are each independently selected from $C_7$ to $C_{19}$ substituted or unsubstituted alkyl or alkenyl;

$R_1$ is a substituted or unsubstituted $C_1$-$C_4$ alkyl;

$R_2$ is independently for each occurrence, H, alkyl, substituted alkyl or N-linked amino acid residue; and m and n are each independently an integer from 0 to 5.

In a first aspect of this embodiment, —OP(=O)(OH)$_2$— and B is —OH.

In a second aspect of this embodiment, D, E, F and G are each OH.

In a third aspect of this embodiment, —OP(=O)(OH)$_2$— and B is —OH and D, E, F and G are each OH.

In any of the first through third aspects of this embodiment, $A_1$, $A_2$, and $A_4$ are each independently a $C_9$ to $C_{13}$ unsubstituted alkyl and $A_3$ and $A_5$ are each independently a $C_{11}$ to $C_{15}$ unsubstituted alkyl.

In any of the first through third aspects of this embodiment, $A_1$, $A_2$, and $A_4$ are each $C_{11}$ unsubstituted alkyl and $A_3$ and $A_5$ are each $C_{13}$ unsubstituted alkyl.

In any of the first through third aspects of this embodiment, $A_1$, $A_2$, and $A_4$ are each $C_{11}$ unsubstituted alkyl, $A_3$ is $C_{11}$ unsubstituted alkyl and $A_5$ is a $C_{13}$ unsubstituted alkyl.

In still another embodiment, such synthetic disaccharide lipid compounds have the general structure shown in formula IV:

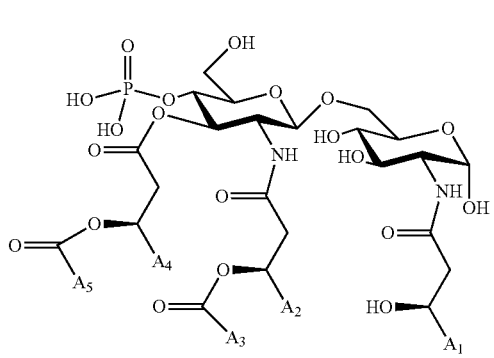

or a pharmaceutically acceptable salt or prodrug thereof, wherein:

$A_1$, $A_2$, and $A_4$ are each independently selected from $C_6$ to $C_{18}$ substituted or unsubstituted alkyl or alkenyl; and $A_3$ and $A_5$ are each independently selected from $C_7$ to $C_{19}$ substituted or unsubstituted alkyl or alkenyl.

In a first aspect of this embodiment, $A_1$, $A_2$, and $A_4$ are each independently a $C_9$ to $C_{13}$ unsubstituted alkyl and $A_3$ and $A_5$ are each independently a $C_{11}$ to $C_{15}$ unsubstituted alkyl.

In a second aspect of this embodiment, $A_1$, $A_2$, and $A_4$ are each $C_{11}$ unsubstituted alkyl and $A_3$ and $A_5$ are each $C_{13}$ unsubstituted alkyl.

In a third aspect of this embodiment, $A_1$, $A_2$, and $A_4$ are each $C_{11}$ unsubstituted alkyl, $A_3$ is $C_{11}$ unsubstituted alkyl and $A_5$ is a $C_{13}$ unsubstituted alkyl.

In yet another embodiment, such synthetic disaccharide lipid compound has the structure shown in formula V:

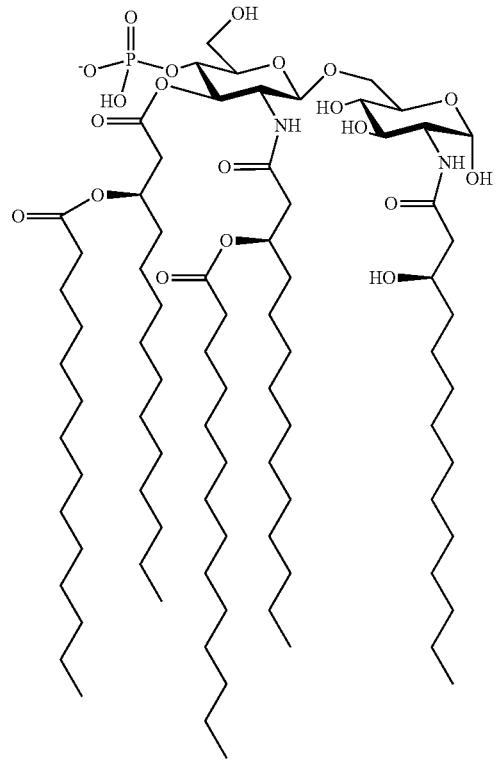

or a pharmaceutically acceptable salt or prodrug thereof.

In one embodiment, such synthetic disaccharide lipid compounds have the general structure shown in formula VI:

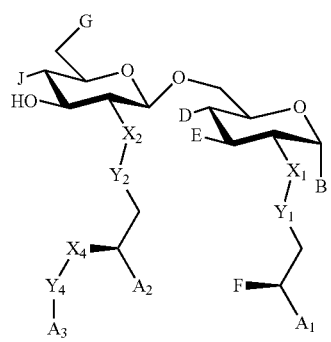

or a pharmaceutically acceptable salt or prodrug thereof, wherein:

$X_1$, $X_2$ and $X_4$ are each independently selected from $C_1$-$C_8$ alkyl, —O—, —NH— or —$CH_2$—;

$Y_1$, $Y_2$ and $Y_4$ are each independently selected from —$CH_2$—, or —C(=O)—;

D, E, G and F are each independently selected from $C_1$-$C_4$ alkyl, —OH, —SH, —OC(=O)($CH_2$)$_m$—$CH_3$, OC(=O)($CH_2$)$_n$C(=O)OH or —OC(=O)CH($NH_2$)($CH_2$)$_n$C(=O)OH;

J and B are each independently selected from OH, $OR_1$, H, —OP(=O)(OH)$_2$—, OP(=O)(OR$_2$)$_2$—, —OS(=O)(OH)$_2$—, —OS(=O)(OR$_2$)$_2$—, —OS(OH)$_2$—, —OS(OR$_2$)$_2$—, —C(=O)OH—, —C(=O)OR$_2$— or an acidic group;

$A_1$ and $A_2$ are each independently selected from $C_6$ to $C_{18}$ substituted or unsubstituted alkyl or alkenyl;

$A_3$ is selected from $C_7$ to $C_{19}$ substituted or unsubstituted alkyl or alkenyl;

$R_1$ is a substituted or unsubstituted $C_1$-$C_4$ alkyl;

$R_2$ is independently for each occurrence, H, alkyl, substituted alkyl or N-linked amino acid residue; and m and n are each independently an integer from 0 to 5.

The foregoing structure VI is derived from that shown in structure I where the group $X_3$ is O, the $Y_3$ is H and the groups attached to $Y_3$ ($X_5$, $Y_5$, $A_5$ and $A_4$ are absent).

In first aspect of this embodiment, at least one of $X_1$ and $X_2$ are —NH—, or both of $X_1$ and $X_2$ are —NH—.

In a second aspect of this embodiment, $X_4$ is —O—.

In a third aspect of this embodiment, $X_4$ is —O— and $X_1$ and $X_2$ are —NH—.

In a fourth another aspect of this embodiment, $X_1$, $X_2$ and $X_4$ are as defined in the first through third aspects and at least one of $Y_1$, $Y_2$ and $Y_4$ are —C(=O)—, at least two of $Y_1$, $Y_2$ and $Y_4$ are —C(=O)— or all of $Y_1$, $Y_2$ and $Y_4$ are —C(=O)—.

In a fifth aspect of this embodiment, $X_4$ is —O—, $X_1$ and $X_2$ are —NH— and all of $Y_1$, $Y_2$ and $Y_4$ are —C(=O)—.

In a sixth aspect of this embodiment, $X_1$, $X_2$ and $X_4$ are as defined in the first through fifth aspects, $Y_1$, $Y_2$ and $Y_4$ are as defined in the fourth and fifth aspects and J is —OP(=O)(OH)$_2$— and B is —OH.

In any of the first through sixth aspects of this embodiment, D, E, F and G are each OH.

In any of the first through sixth aspects of this embodiment, $A_1$ $A_2$, and $A_4$ are each independently $C_9$ to $C_{13}$ unsubstituted alkyl and $A_3$ and $A_5$ are each independently are $C_{11}$ to $C_{15}$ unsubstituted alkyl.

In any of the first through sixth aspects of this embodiment, $A_1$ $A_2$, and $A_4$ are each $C_{11}$ unsubstituted alkyl and $A_3$ and $A_5$ are each $C_{13}$ unsubstituted alkyl.

In any of the first through sixth aspects of this embodiment, $A_1$ $A_2$, and $A_4$ are each $C_{11}$ unsubstituted alkyl, $A_3$ is a $C_{11}$ unsubstituted alkyl and $A_5$ is a $C_{13}$ unsubstituted alkyl.

In another embodiment, such synthetic disaccharide lipid compounds have the general structure shown in formula VII:

VII or a pharmaceutically acceptable salt or prodrug thereof, wherein:

$Y_1$, $Y_2$ and $Y_4$ are each independently selected from —$CH_2$—, or —C(=O)—;

D, E, G and F are each independently selected from $C_1$-$C_4$ alkyl, —OH, —SH, —OC(=O)($CH_2$)$_m$—$CH_3$, OC(=O)($CH_2$)$_n$C(=O)OH or —OC(=O)CH($NH_2$)($CH_2$)$_n$C(=O)OH;

J and B are each independently selected from OH, $OR_1$, H, —OP(=O)(OH)$_2$—, OP(=O)($OR_2$)$_2$—, —OS(=O)(OH)$_2$—, —OS(=O)($OR_2$)$_2$—, —OS(OH)$_2$—, —OS($OR_2$)$_2$—, —C(=O)OH—, —C(=O)$OR_2$— or an acidic group;

$A_1$ and $A_2$ are each independently selected from $C_6$ to $C_{18}$ substituted or unsubstituted alkyl or alkenyl;

$A_3$ is selected from $C_7$ to $C_{19}$ substituted or unsubstituted alkyl or alkenyl;

$R_1$ is a substituted or unsubstituted $C_1$-$C_4$ alkyl;

$R_2$ is independently for each occurrence, 1H, alkyl, substituted alkyl or N-linked amino acid residue; and m and n are each independently an integer from 0 to 5.

In a first aspect of this embodiment, at least one of $Y_1$, $Y_2$ and $Y_4$ are —C(=O)—, at least two of $Y_1$, $Y_2$ and $Y_4$ are —C(=O)—, or all of $Y_1$, $Y_2$ and $Y_4$ are —C(=O)—.

In a second aspect of this embodiment, $Y_1$, $Y_2$ and $Y_4$ are as defined in the first aspect and J is —OP(=O)(OH)$_2$— and B is —OH.

In any of the first through second aspects of this embodiment, D, E, F and G are each OH.

In any of the first through second aspects of this embodiment, $A_1$, $A_2$, and $A_4$ are each independently a $C_9$ to $C_{13}$ unsubstituted alkyl and $A_3$ and $A_5$ are each independently a $C_{11}$ to $C_{15}$ unsubstituted alkyl.

In any of the first through second aspects of this embodiment, $A_1$, $A_2$, and $A_4$ are each $C_{11}$ unsubstituted alkyl and $A_3$ and $A_5$ are each $C_{13}$ unsubstituted alkyl.

In any of the first through second aspects of this embodiment, $A_1$, $A_2$, and $A_4$ are each $C_{11}$ unsubstituted alkyl, $A_3$ is $C_{11}$ unsubstituted alkyl and $A_5$ is a $C_{13}$ unsubstituted alkyl.

In still another embodiment, synthetic disaccharide lipid compounds have the general structure shown in formula VIII:

VIII or a pharmaceutically acceptable salt or prodrug thereof, wherein:

D, E, G and F are each independently selected from $C_1$-$C_4$ alkyl, —OH, —SH, —OC(=O)($CH_2$)$_m$, —$CH_3$, OC(=O)($CH_2$)$_n$C(=O)OH or —OC(=O)CH($NH_2$)($CH_2$)$_n$C(=O)OH;

J and B are each independently selected from OH, $OR_1$, H, —OP(=O)(OH)$_2$—, OP(=O)($OR_2$)$_2$—, —OS(=O)(OH)$_2$—, —OS(=O)($OR_2$)$_2$—, —OS(OH)$_2$—, —OS($OR_2$)$_2$—, —C(=O)OH—, —C(=O)$OR_2$— or an acidic group;

$A_1$ and $A_2$ are each independently selected from $C_6$ to $C_{18}$ substituted or unsubstituted alkyl or alkenyl;

$A_3$ is selected from $C_7$ to $C_{19}$ substituted or unsubstituted alkyl or alkenyl;

$R_1$ is a substituted or unsubstituted $C_1$-$C_4$ alkyl;

$R_2$ is independently for each occurrence, H, alkyl, substituted alkyl or N-linked amino acid residue; and m and n are each independently an integer from 0 to 5.

In a first aspect of this embodiment, J is —OP(=O)(OH)$_2$— and B is —OH.

In a second aspect of this embodiment, D, E, F and G are each OH.

In a third aspect of this embodiment, J is —OP(=O)(OH)$_2$— and B is —OH and D, E, F and G are each OH.

In any of the first through third aspects of this embodiment, $A_1$, $A_2$, and $A_4$ are each independently a $C_9$ to $C_{13}$ unsubstituted alkyl and $A_3$ and $A_5$ are each independently a $C_{11}$ to $C_{15}$ unsubstituted alkyl.

In any of the first through third aspects of this embodiment, $A_1$, $A_2$, and $A_4$ are each $C_{11}$ unsubstituted alkyl and $A_3$ and $A_5$ are each $C_{13}$ unsubstituted alkyl.

In any of the first through third aspects of this embodiment, $A_1$, $A_2$, and $A_4$ are each $C_{11}$ unsubstituted alkyl, $A_3$ is $C_{11}$ unsubstituted alkyl and $A_5$ is a $C_{13}$ unsubstituted alkyl.

In still another embodiment, such synthetic disaccharide lipid compounds have the general structure shown in formula IX:

IX or a pharmaceutically acceptable salt or prodrug thereof, wherein:

$A_1$, $A_2$, and $A_4$ are each independently selected from $C_6$ to $C_{18}$ substituted or unsubstituted alkyl or alkenyl; and $A_3$ and $A_5$ are each independently selected from $C_7$ to $C_{19}$ substituted or unsubstituted alkyl or alkenyl.

In a first aspect of this embodiment, $A_1$, $A_2$, and $A_4$ are each independently a $C_9$ to $C_{13}$ unsubstituted alkyl and $A_3$ and $A_5$ are each independently a $C_{11}$ to $C_{15}$ unsubstituted alkyl.

In a second aspect of this embodiment, $A_1$, $A_2$, and $A_4$ are each $C_{11}$ unsubstituted alkyl and $A_3$ and $A_5$ are each $C_{13}$ unsubstituted alkyl.

In a third aspect of this embodiment, $A_1$, $A_2$, and $A_4$ are each $C_{11}$ unsubstituted alkyl, $A_3$ is $C_{11}$ unsubstituted alkyl and $A_5$ is a $C_{13}$ unsubstituted alkyl.

In yet another embodiment, such synthetic disaccharide lipid compound has the structure shown in formula X:

X or a pharmaceutically acceptable salt or prodrug thereof.

In one embodiment, such synthetic disaccharide lipid compounds have the general structure shown in formula XI:

XI or a pharmaceutically acceptable salt or prodrug thereof, wherein:

$X_1$, $X_2$, $X_3$, $X_4$ and $X_5$ are each independently absent or selected from $C_1$-$C_8$ alkyl, —O—, —NH— or —CH$_2$—;

$Y_1$, $Y_2$, $Y_3$ and $Y_4$ are each independently selected from —CH$_2$—, or —C(=O)—;

$Y_5$ is H or $C_1$-$C_4$ alkyl;

D, E, G and F are each independently selected from $C_1$-$C_4$ alkyl, —OH, —SH, —OC(=O)(CH$_2$)$_m$—CH$_3$, OC(=O)(CH$_2$)$_n$C(=O)OH or —OC(=O)CH(NH$_2$)(CH$_2$)$_n$C(=O)OH;

J and B are each independently selected from OH, OR$_1$, H, —OP(=O)(OH)$_2$—, OP(=O)(OR$_2$)$_2$—, —OS(=O)(OH)$_2$—, —OS(=O)(OR$_2$)$_2$—, —OS(OH)$_2$—, —OS(OR$_2$)$_2$—, —C(=O)OH—, —C(=O)OR$_2$— or an acidic group;

$A_1$, $A_2$ and $A_4$ are each independently selected from $C_6$ to $C_{18}$ substituted or unsubstituted alkyl or alkenyl;

$A_3$ is selected from $C_7$ to $C_{19}$ substituted or unsubstituted alkyl or alkenyl;

$R_1$ is a substituted or unsubstituted $C_1$-$C_4$ alkyl;

$R_2$ is independently for each occurrence, H, alkyl, substituted alkyl or N-linked amino acid residue; and m and n are each independently an integer from 0 to 5.

The foregoing structure XI is derived from that shown in structure I where the group $X_5$ is O, $Y_5$ is H and the groups attached to $Y_5$ ($A_5$ is absent).

In first aspect of this embodiment, at least one of $X_3$, $X_4$ and $X_5$ are —O—, at least two of $X_3$, $X_4$ and $X_5$ are —O—, or all three of $X_3$, $X_4$ and $X_5$ are —O—.

In a second aspect of this embodiment, at least one of $X_1$ and $X_2$ are —NH—, or both of $X_1$ and $X_2$ are —NH—.

In a third aspect of this embodiment, $X_3$, $X_4$ and $X_5$ are —O— and $X_1$ and $X_2$ are —NH—.

In a fourth another aspect of this embodiment, $X_1$ to $X_5$ are as defined in the first through third aspects, at least one of $Y_1$, $Y_2$, $Y_3$ and $Y_4$ are —C(=O)—, at least two of $Y_1$, $Y_2$, $Y_3$ and $Y_4$ are —C(=O)—, at least three of $Y_1$, $Y_2$, $Y_3$ and $Y_4$ are —C(=O)— or all of $Y_1$, $Y_2$, $Y_3$ and $Y_4$ are —C(=O) and $Y_5$ is H.

In a fifth aspect of this embodiment, $X_3$, $X_4$ and $X_5$ are —O—, $X_1$ and $X_2$ are —NH— and all of $Y_1$, $Y_2$, $Y_3$ and $Y_4$ are —C(=O)— and $Y_5$ is H.

In a sixth aspect of this embodiment, $X_1$ to $X_5$ are as defined in the first through fifth aspects, $Y_1$ to $Y_5$ are as defined in the fourth and fifth aspects and J is —OP(=O)(OH)$_2$— and B is —OH.

In any of the first through sixth aspects of this embodiment, D, E, F and G are each OH.

In any of the first through sixth aspects of this embodiment, $A_1$, $A_2$, and $A_4$ are each independently $C_9$ to $C_{13}$ unsubstituted alkyl and $A_3$ is a $C_{11}$ to $C_{15}$ unsubstituted alkyl.

In any of the first through sixth aspects of this embodiment, $A_1$, $A_2$, and $A_4$ are each $C_{11}$ unsubstituted alkyl and $A_3$ is $C_{13}$ unsubstituted alkyl.

In another embodiment, such synthetic disaccharide lipid compounds have the general structure shown in formula XII:

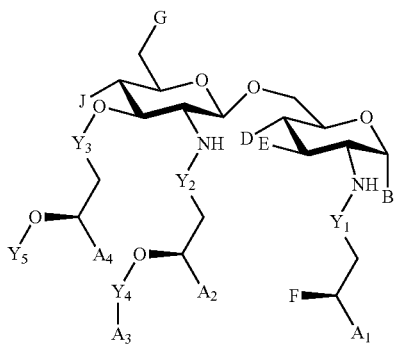

XII or a pharmaceutically acceptable salt or prodrug thereof, wherein:

$Y_1$, $Y_2$, $Y_3$ and $Y_4$ are each independently selected from —$CH_2$—, or —C(=O)—;

$Y_5$ is H or $C_1$-$C_4$ alkyl;

D, E, G and F are each independently selected from $C_1$-$C_4$ alkyl, —OH, —SH, —OC(=O)($CH_2$)$_m$—$CH_3$, OC(=O)($CH_2$)$_n$C(=O)OH or —OC(=O)CH($NH_2$)($CH_2$)$_n$C(=O)OH;

J and B are each independently selected from OH, $OR_1$, H, —OP(=O)(OH)$_2$—, OP(=O)($OR_2$)$_2$—, —OS(=O)(OH)$_2$—, —OS(=O)($OR_2$)$_2$—, —OS(OH)$_2$—, —OS($OR_2$)$_2$—, —C(=O)OH—, —C(=O)$OR_2$— or an acidic group;

$A_1$, $A_2$ and $A_4$ are each independently selected from $C_6$ to $C_{18}$ substituted or unsubstituted alkyl or alkenyl;

$A_3$ is selected from $C_7$ to $C_{19}$ substituted or unsubstituted alkyl or alkenyl;

$R_1$ is a substituted or unsubstituted $C_1$-$C_4$ alkyl;

$R_2$ is independently for each occurrence, H, alkyl, substituted alkyl or N-linked amino acid residue; and m and n are each independently an integer from 0 to 5.

In a first aspect of this embodiment, at least one of $Y_1$, $Y_2$, $Y_3$ and $Y_4$ are —C(=O)—, at least two of $Y_1$, $Y_2$, $Y_3$ and $Y_4$ are —C(=O)—, at least three of $Y_1$, $Y_2$ $Y_3$ and $Y_4$ are —C(=O) or all of $Y_1$, $Y_2$, $Y_3$ and $Y_4$ are —C(=O)— and $Y_5$ is H.

In a second aspect of this embodiment, $Y_1$ to $Y_5$ are as defined in the first aspect and J is —OP(=O)(OH)$_2$— and B is —OH.

In any of the first through second aspects of this embodiment, D, E, F and G are each OH.

In any of the first through second aspects of this embodiment, $A_1$, $A_2$, and $A_4$ are each independently a $C_9$ to $C_{13}$ unsubstituted alkyl and $A_3$ is a $C_{11}$ to $C_{15}$ unsubstituted alkyl.

In any of the first through second aspects of this embodiment, $A_1$, $A_2$, and $A_4$ are each $C_{11}$ unsubstituted alkyl and $A_3$ is a $C_{13}$ unsubstituted alkyl.

In still another embodiment, synthetic disaccharide lipid compounds have the general structure shown in formula XIII:

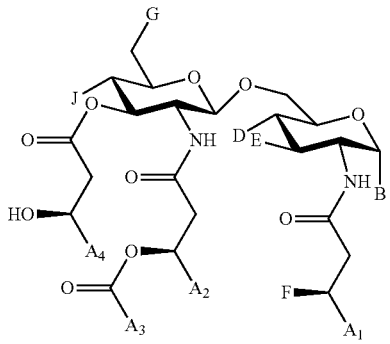

XIII or a pharmaceutically acceptable salt or prodrug thereof, wherein:

D, E, G and F are each independently selected from $C_1$-$C_4$ alkyl, —OH, —SH, —OC(=O)($CH_2$)$_m$—$CH_3$, OC(=O)($CH_2$)$_n$C(=O)OH or —OC(=O)CH($NH_2$)($CH_2$)$_n$C(=O)OH;

J and B are each independently selected from OH, $OR_1$, H, —OP(=O)(OH)$_2$—, OP(=O)($OR_2$)$_2$—, —OS(=O)(OH)$_2$—, —OS(=O)($OR_2$)$_2$—, —OS(OH)$_2$—, —OS($OR_2$)$_2$—, —C(=O)OH—, —C(=O)$OR_2$— or an acidic group;

$A_1$, $A_2$ and $A_4$ are each independently selected from $C_6$ to $C_{18}$ substituted or unsubstituted alkyl or alkenyl;

$A_3$ is selected from $C_7$ to $C_{19}$ substituted or unsubstituted alkyl or alkenyl;

$R_1$ is a substituted or unsubstituted $C_1$-$C_4$ alkyl;

$R_2$ is independently for each occurrence, H, alkyl, substituted alkyl or N-linked amino acid residue; and m and n are each independently an integer from 0 to 5.

In a first aspect of this embodiment, J is —OP(=O)(OH)$_2$— and B is —OH.

In a second aspect of this embodiment, D, E, F and G are each OH.

In a third aspect of this embodiment, J is —OP(=O)(OH)$_2$— and B is —OH and D, E, F and G are each OH.

In any of the first through third aspects of this embodiment, $A_1$, $A_2$, and $A_4$ are each independently a $C_9$ to $C_{13}$ unsubstituted alkyl $A_3$ is a $C_{11}$ to $C_{15}$ unsubstituted alkyl.

In any of the first through third aspects of this embodiment, $A_1$, $A_2$, and $A_4$ are each $C_{11}$ unsubstituted alkyl, $A_3$ is a $C_{13}$ unsubstituted alkyl.

In still another embodiment, such synthetic disaccharide lipid compounds have the general structure shown in formula XIV:

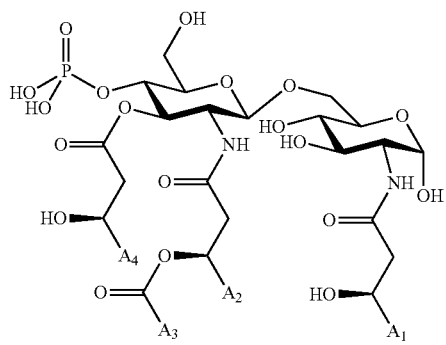

XIV or a pharmaceutically acceptable salt or prodrug thereof, wherein:

$A_1$, $A_2$, and $A_4$ are each independently selected from $C_6$ to $C_{18}$ substituted or unsubstituted alkyl or alkenyl; and $A_3$ is selected from $C_7$ to $C_{19}$ substituted or unsubstituted alkyl or alkenyl In a first aspect of this embodiment, $A_1$, $A_2$, and $A_4$ are each independently a $C_9$ to $C_{13}$ unsubstituted alkyl and $A_3$ is a $C_{11}$ to $C_{15}$ unsubstituted alkyl.

In a second aspect of this embodiment, $A_1$, $A_2$, and $A_4$ are each $C_{11}$ unsubstituted alkyl and $A_3$ is a $C_{13}$ unsubstituted alkyl.

In yet another embodiment, such synthetic disaccharide lipid compound has the structure shown in formula XV:

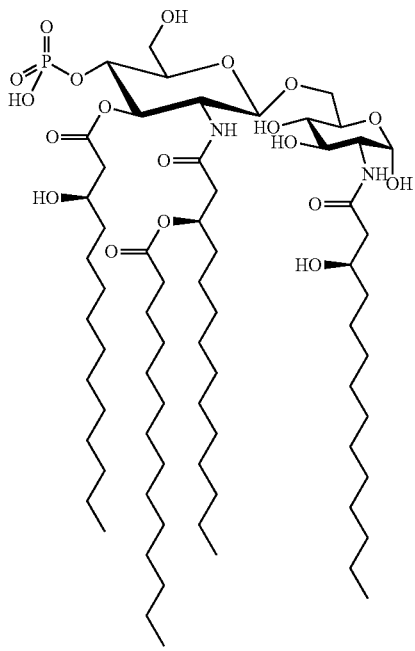

XV or a pharmaceutically acceptable salt or prodrug thereof.

In one embodiment, such synthetic disaccharide lipid compounds have the general structure shown in formula XVI:

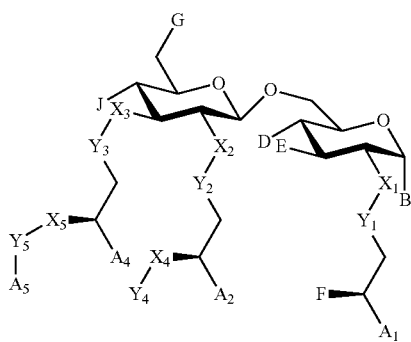

XVI or a pharmaceutically acceptable salt or prodrug thereof, wherein:

$X_1$, $X_2$, $X_3$, $X_4$ and $X_5$ are each independently absent or selected from $C_1$-$C_8$ alkyl, —O—, —NH— or —CH$_2$—;

$Y_1$, $Y_2$, $Y_3$ and $Y_5$ are each independently selected from —CH$_2$—, or —C(=O)—;

$Y_4$ is H or $C_1$-$C_4$ alkyl;

D, E, G and F are each independently selected from $C_1$-$C_4$ alkyl, —OH, —SH, —OC(=O)(CH$_2$)$_m$—CH$_3$, —OC(=O)(CH$_2$)$_n$C(=O)OH or —OC(=O)CH(NH$_2$)(CH$_2$)$_n$C(=O)OH;

J and B are each independently selected from OH, OR$_1$, H, —OP(=O)(OH)$_2$—, —OP(=O)(OR$_2$)$_2$—, —OS(=O)(OH)$_2$—, —OS(=O)(OR$_2$)$_2$—, —OS(OH)$_2$—, —OS(OR$_2$)$_2$—, —C(=O)OH—, —C(=O)OR$_2$— or an acidic group;

$A_1$, $A_2$ and $A_4$ are each independently selected from $C_6$ to $C_{18}$ substituted or unsubstituted alkyl or alkenyl;

$A_5$ is selected from $C_7$ to $C_{19}$ substituted or unsubstituted alkyl or alkenyl;

$R_1$ is a substituted or unsubstituted $C_1$-$C_4$ alkyl;

$R_2$ is independently for each occurrence, H, alkyl, substituted alkyl or N-linked amino acid residue; and m and n are each independently an integer from 0 to 5.

The foregoing structure XVI is derived from that shown in structure I where the group $X_4$ is O, $Y_4$ is H and the groups attached to $Y_4$ ($A_3$) are absent.

In first aspect of this embodiment, at least one of $X_3$, $X_4$ and $X_5$ are —O—, at least two of $X_3$, $X_4$ and $X_5$ are —O—, or all three of $X_3$, $X_4$ and $X_5$ are —O—.

In a second aspect of this embodiment, at least one of $X_1$ and $X_2$ are —NH—, or both of $X_1$ and $X_2$ are —NH—.

In a third aspect of this embodiment, $X_3$, $X_4$ and $X_5$ are —O— and $X_1$ and $X_2$ are —NH—.

In a fourth another aspect of this embodiment, $X_1$ to $X_5$ are as defined in the first through third aspects, at least one of $Y_1$, $Y_2$, $Y_3$ and $Y_3$ are —C(=O)—, at least two of $Y_1$, $Y_2$, $Y_3$ and $Y_5$ are —C(=O)—, at least three of $Y_1$, $Y_2$, $Y_3$ and $Y_5$ are —C(=O)— or all of $Y_1$, $Y_2$, $Y_3$ and $Y_5$ are —C(=O) and $Y_4$ is H.

In a fifth aspect of this embodiment, $X_3$, $X_4$ and $X_5$ are —O—, $X_1$ and $X_2$ are —NH— and all of $Y_1$, $Y_2$, $Y_3$ and $Y_5$ are —C(=O)— and $Y_4$ is H.

In a sixth aspect of this embodiment, $X_1$ to $X_5$ are as defined in the first through fifth aspects, $Y_1$ to $Y_5$ are as defined in the fourth and fifth aspects and J is —OP(=O)(OH)$_2$— and B is —OH.

In any of the first through sixth aspects of this embodiment, D, E, F and G are each OH.

In any of the first through sixth aspects of this embodiment, $A_1$ $A_2$, and $A_4$ are each independently $C_9$ to $C_{13}$ unsubstituted alkyl and $A_5$ is a $C_{11}$ to $C_{15}$ unsubstituted alkyl.

In any of the first through sixth aspects of this embodiment, $A_1$ $A_2$, and $A_4$ are each $C_{11}$ unsubstituted alkyl and $A_5$ is $C_{13}$ unsubstituted alkyl.

In another embodiment, such synthetic disaccharide lipid compounds have the general structure shown in formula XVII:

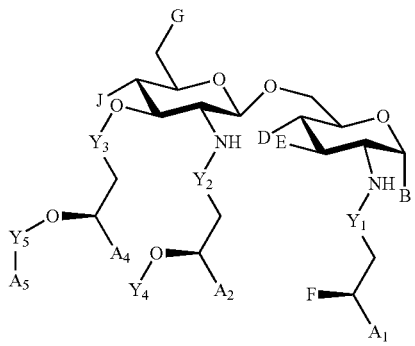

XVII

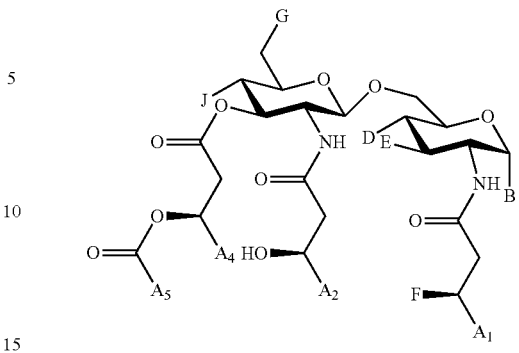

XVIII or a pharmaceutically acceptable salt or prodrug thereof, wherein:

$Y_1$, $Y_2$, $Y_3$ and $Y_5$ are each independently selected from —$CH_2$—, or —C(=O)—;

$Y_4$ is H or $C_1$-$C_4$ alkyl;

D, E, G and F are each independently selected from $C_1$-$C_4$ alkyl, —OH, —SH, —OC(=O)($CH_2$)$_m$—$CH_3$, OC(=O)($CH_2$)$_n$C(=O)OH or —OC(=O)CH($NH_2$)($CH_2$)$_n$C(=O)OH;

J and B are each independently selected from OH, $OR_1$, H, —OP(=O)(OH)$_2$—, OP(=O)($OR_2$)$_2$—, —OS(=O)(OH)$_2$—, —OS(=O)($OR_2$)$_2$—, —OS(OH)$_2$—, —OS($OR_2$)$_2$—, —C(=O)OH—, —C(=O)$OR_2$— or an acidic group;

$A_1$, $A_2$ and $A_4$ are each independently selected from $C_6$ to $C_{18}$ substituted or unsubstituted alkyl or alkenyl;

$A_5$ is selected from $C_7$ to $C_{19}$ substituted or unsubstituted alkyl or alkenyl;

$R_1$ is a substituted or unsubstituted $C_1$-$C_4$ alkyl;

$R_2$ is independently for each occurrence, H, alkyl, substituted alkyl or N-linked amino acid residue; and m and n are each independently an integer from 0 to 5.

In a first aspect of this embodiment, at least one of $Y_1$, $Y_2$, $Y_3$ and $Y_5$ are —C(=O)—, at least two of $Y_1$, $Y_2$, $Y_3$ and $Y_5$ are —C(=O)—, at least three of $Y_1$, $Y_2$ $Y_4$ and $Y_5$ are —C(=O) or all of $Y_1$, $Y_2$, $Y_3$ and $Y_5$ are —C(=O)— and $Y_4$ is H.

In a second aspect of this embodiment, $Y_1$, to $Y_5$ are as defined in the first aspect and J is —OP(=O)(OH)$_2$— and B is —OH.

In any of the first through second aspects of this embodiment, D, E, F and G are each OH.

In any of the first through second aspects of this embodiment, $A_1$, $A_2$, and $A_4$ are each independently a $C_9$ to $C_{13}$ unsubstituted alkyl and $A_5$ is a $C_{11}$ to $C_{15}$ unsubstituted alkyl.

In any of the first through second aspects of this embodiment, $A_1$, $A_2$, and $A_4$ are each $C_{11}$ unsubstituted alkyl and $A_5$ is a $C_{13}$ unsubstituted alkyl.

In still another embodiment, synthetic disaccharide lipid compounds have the general structure shown in formula XVIII:

or a pharmaceutically acceptable salt or prodrug thereof, wherein:

D, E, G and F are each independently selected from $C_1$-$C_4$ alkyl, —OH, —SH, —OC(=O)($CH_2$)$_m$—$CH_3$, OC(=O)($CH_2$)$_n$C(=O)OH or —OC(=O)CH($NH_2$)($CH_2$)$_n$C(=O)OH;

J and B are each independently selected from OH, $OR_1$, H, —OP(=O)(OH)$_2$—, OP(=O)($OR_2$)$_2$—, —OS(=O)(OH)$_2$—, —OS(=O)($OR_2$)$_2$—, —OS(OH)$_2$—, —OS($OR_2$)$_2$—, —C(=O)OH—, —C(=O)$OR_2$— or an acidic group;

$A_1$, $A_2$ and $A_4$ are each independently selected from $C_6$ to $C_{18}$ substituted or unsubstituted alkyl or alkenyl;

$A_5$ is selected from $C_7$ to $C_{19}$ substituted or unsubstituted alkyl or alkenyl;

$R_1$ is a substituted or unsubstituted $C_1$-$C_4$ alkyl;

$R_2$ is independently for each occurrence, H, alkyl, substituted alkyl or N-linked amino acid residue; and m and n are each independently an integer from 0 to 5.

In a first aspect of this embodiment, J is —OP(=O)(OH)$_2$— and B is —OH.

In a second aspect of this embodiment, D, E, F and G are each OH.

In a third aspect of this embodiment, J is —OP(=O)(OH)$_2$— and B is —OH and D, E, F and G are each OH.

In any of the first through third aspects of this embodiment, $A_1$, $A_2$, and $A_4$ are each independently a $C_9$ to $C_{13}$ unsubstituted alkyl $A_5$ is a $C_{11}$ to $C_{15}$ unsubstituted alkyl.

In any of the first through third aspects of this embodiment, $A_1$, $A_2$, and $A_4$ are each $C_{11}$ unsubstituted alkyl, $A_5$ is a $C_{13}$ unsubstituted alkyl.

In still another embodiment, such synthetic disaccharide lipid compounds have the general structure shown in formula XIX:

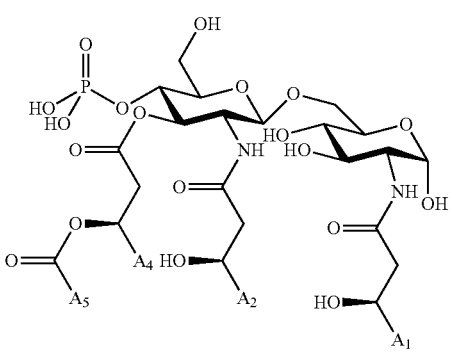

XIX or a pharmaceutically acceptable salt or prodrug thereof, wherein:

$A_1$, $A_2$, and $A_4$ are each independently selected from $C_6$ to $C_{18}$ substituted or unsubstituted alkyl or alkenyl; and $A_5$ is selected from $C_7$ to $C_{19}$ substituted or unsubstituted alkyl or alkenyl In a first aspect of this embodiment, $A_1$, $A_2$, and $A_4$ are each independently a $C_9$ to $C_{13}$ unsubstituted alkyl and $A_5$ is a $C_{11}$ to $C_{15}$ unsubstituted alkyl.

In a second aspect of this embodiment, $A_1$, $A_2$, and $A_4$ are each $C_{11}$ unsubstituted alkyl and $A_5$ is a $C_{13}$ unsubstituted alkyl.

In yet another embodiment, such synthetic disaccharide lipid compound has the structure shown in formula XX:

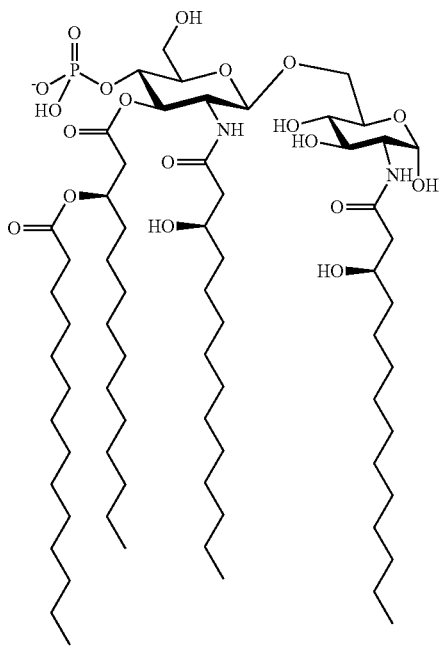

XX or a pharmaceutically acceptable salt or prodrug thereof.

Methods of Using the Compounds of the Present Disclosure

The present disclosure shows that disaccharide synthetic lipid compounds may be prepared in an essentially pure form. Therefore, the provision of an essentially pure synthetic disaccharide lipid compounds of the present disclosure allows for methods of stimulating an immune response in a subject that are free from the disadvantages of the compounds known in the art.

In one embodiment, the present disclosure provides methods for stimulating or eliciting an immune response in a subject. Such method comprises the step of administering to the subject an amount of a synthetic disaccharide lipid compound of the present disclosure or a pharmacologically acceptable salt thereof. In one aspect, the synthetic disaccharide lipid compound or a pharmacologically acceptable salt thereof is administered alone. In another aspect, the synthetic disaccharide lipid compound or a pharmacologically acceptable salt thereof is administered with a second adjuvant or additional adjuvants. In another aspect, the synthetic disaccharide lipid compound or a pharmacologically acceptable salt thereof is administered with an antigen. In another aspect, the synthetic disaccharide lipid compound or a pharmacologically acceptable salt thereof is administered with an antigen and a second adjuvant or additional adjuvants. In one embodiment, such administration increases an immune response in a subject. When an antigen is included, such administration increases an immune response in a subject that is specific, at least in part, to the antigen delivered.

In one embodiment, the present disclosure provides methods for enhancing an immune response in a subject. Such method comprises the step of administering to the subject an amount of a synthetic disaccharide lipid compound of the present disclosure or a pharmacologically acceptable salt thereof. In one aspect, a synthetic disaccharide lipid compound or a pharmacologically acceptable salt thereof is administered alone. In another aspect, the synthetic disaccharide lipid compound or a pharmacologically acceptable salt thereof is administered with a second adjuvant or additional adjuvants. In another aspect, the synthetic disaccharide lipid compound or a pharmacologically acceptable salt thereof is administered with an antigen. In another aspect, the synthetic disaccharide lipid compound or a pharmacologically acceptable salt thereof is administered with an antigen and a second adjuvant or additional adjuvants. In one embodiment, such administration enhances an immune response in a subject. When an antigen is included, such administration enhances an immune response in a subject that is specific, at least in part, to the antigen delivered.

In one embodiment, the present disclosure provides methods for stimulating immunoglobulin production in a subject. In one embodiment, the immunoglobulin is IgG. In another embodiment, the immunoglobulin is IgM. Such method comprises the step of administering to the subject an amount of a synthetic disaccharide lipid compound of the present disclosure or a pharmacologically acceptable salt thereof. In one aspect, a synthetic disaccharide lipid compound or a pharmacologically acceptable salt thereof is administered alone. In another aspect, the synthetic disaccharide lipid compound or a pharmacologically acceptable salt thereof is administered with a second adjuvant or additional adjuvants. In another aspect, the synthetic disaccharide lipid compound or a pharmacologically acceptable salt thereof is administered with an antigen. In another aspect, the synthetic disaccharide lipid compound or a pharmacologically acceptable salt thereof is administered with an antigen and a second adjuvant or additional adjuvants. In one embodiment, such administration stimulates or enhances an immune response in a subject. When an antigen is included, the immunoglobulin produced may be specific to the antigen delivered.

Toll-Like Receptors (TLRs), including TLR4, are pattern-recognition receptors (PRRs). TLRs play a well-known role in the initiation of immune responses. At least 10 functional TLRs have been identified in humans. Each TLR detects distinct pathogen associated molecular patterns derived from viruses, bacteria, mycobacteria, fungi, and parasites. Gram-negative bacteria are typically sensed through the cell wall constituent lipopolysaccharide (LPS) that binds in complex with the LPS-binding Protein (LBP) to a receptor complex of TLR4, CD14 and an associated protein (MD-2). The TLR4-mediated signalling cascades then modulate the gene expression towards the production of a variety of pro-inflammatory cytokines such as Interleukin (IL)-6, Tumour necrosis factor (TNF)-α and IL-12. In addition, these signalling events enhance the co-stimulatory function of monocytes.

In one embodiment, the present disclosure provides methods for stimulating TLR4 and/or stimulating a TLR4 response. Stimulating a TLR4 response includes stimulating TLR4 signaling. Such method comprises the step of administering to the subject an amount of a synthetic disaccharide lipid compound of the present disclosure or a pharmacologically acceptable salt thereof. In one aspect, the synthetic disaccharide lipid compound or a pharmacologically acceptable salt thereof is administered alone. In another aspect, the synthetic disaccharide lipid compound or a pharmacologically acceptable salt thereof is administered with a second adjuvant or additional adjuvants. In another aspect, the synthetic disaccharide lipid compound or a pharmacologically acceptable salt thereof is administered with an antigen. In another aspect, the synthetic disaccharide lipid compound or a pharmacologically acceptable salt thereof is administered with an antigen and a second adjuvant or additional adjuvants. In one embodiment, such administration stimulates or enhances an immune response in a subject. When an antigen is included, such administration stimulates or enhances an immune response in a subject that is specific, at least in part, to the antigen delivered.

In one aspect of these embodiments, the present disclosure provides for monotherapy using a synthetic disaccharide lipid compound of the present disclosure alone (i.e., without the addition of an antigen or other immune response modifiers). In such an aspect, the synthetic disaccharide lipid compound stimulates a non-specific immune response in a subject for the purpose of treating and/or preventing a disease or condition in a subject.

In one aspect of these embodiments, the present disclosure provides for therapy using a synthetic disaccharide lipid compound of the present disclosure in combination with a second adjuvant (but without the addition of an antigen). In such an aspect, the synthetic disaccharide lipid compound and second adjuvant stimulates a non-specific immune response in a subject for the purpose of treating and/or preventing a disease or condition in a subject.

In one aspect of these embodiments, the present disclosure provides for a pharmaceutical composition, such as a vaccine, comprising a synthetic disaccharide lipid compound of the present disclosure in combination with an antigen and an optional second adjuvant and other components as described herein. In such an aspect, the pharmaceutical composition stimulates a specific immune response in a subject for the purpose of treating and/or preventing a disease or condition in a subject.

In one aspect of these embodiments, the synthetic disaccharide lipid compound is a compound of the general formula (I). In another aspect of these embodiments, the synthetic disaccharide lipid compound is a compound of the general formula (II). In another aspect of these embodiments, the synthetic disaccharide lipid compound is a compound of the general formula (III). In another aspect of these embodiments, the synthetic disaccharide lipid compound is a compound of the general formula (IV). In another aspect of these embodiments, the synthetic disaccharide lipid compound is a compound of the general formula (V). In another aspect of these embodiments, the synthetic disaccharide lipid compound is a compound of the general formula (VI). In another aspect of these embodiments, the synthetic disaccharide lipid compound is a compound of the general formula (VII). In another aspect of these embodiments, the synthetic disaccharide lipid compound is a compound of the general formula (VII). In another aspect of these embodiments, the synthetic disaccharide lipid compound is a compound of the general formula (IX). In another aspect of these embodiments, the synthetic disaccharide lipid compound is a compound of the general formula (X). In another aspect of these embodiments, the synthetic disaccharide lipid compound is a compound of the general formula (XI). In another aspect of these embodiments, the synthetic disaccharide lipid compound is a compound of the general formula (XII). In another aspect of these embodiments, the synthetic disaccharide lipid compound is a compound of the general formula (XII). In another aspect of these embodiments, the synthetic disaccharide lipid compound is a compound of the general formula (XIV). In another aspect of these embodiments, the synthetic disaccharide lipid compound is a compound of the general formula (XV). In another aspect of these embodiments, the synthetic disaccharide lipid compound is a compound of the general formula (XVI). More than one synthetic disaccharide lipid compound may be used in the recited methods if desired. In another aspect of these embodiments, the synthetic disaccharide lipid compound is a compound of the general formula (XVII). In another aspect of these embodiments, the synthetic disaccharide lipid compound is a compound of the general formula (XVIII). In another aspect of these embodiments, the synthetic disaccharide lipid compound is a compound of the general formula (XIX). In another aspect of these embodiments, the synthetic disaccharide lipid compound is a compound of the general formula (XX).

In one aspect of these embodiments, the synthetic disaccharide lipid compound is a compound of the general formula (V), (X), (XV) or (XX). In one aspect of these embodiments, the synthetic disaccharide lipid compound is a compound of the general formula (V). In one aspect of these embodiments, the synthetic disaccharide lipid compound is a compound of the general formula (X). In one aspect of these embodiments, the synthetic disaccharide lipid compound is a compound of the general formula (XV). In one aspect of these embodiments, the synthetic disaccharide lipid compound is a compound of the general formula (XX).

In one aspect of these embodiments, the second adjuvant is any compound that has an immunostimulatory effect that is not a synthetic disaccharide lipid compound of the present disclosure. As used herein, the term immunostimulatory and similar terms means that a compound or composition provides agent enhances a subject's immune response, either in a general manner or in response to an antigen.

In one aspect of these embodiments, the second adjuvant is Monophosphoryl Lipid A (also known as mono-phosphorylated hexaacyl disaccharide and PHAD™) (Avanti Polar Lipids, Alabaster Ala.; catalogue number 699800). In another aspect of these embodiments, the second adjuvant is a TLR agonist.

In one aspect of these embodiments, the synthetic disaccharide lipid compound may be administered alone or as a part of a pharmaceutical composition as described herein. A single compound of the general formula (I) to (XX) may be administered; multiple compounds of the general formula (I) to (XX) may be administered.

In one aspect of these embodiments, the subject is determined to be in need of such treatment. In a further aspect of these embodiments, the synthetic disaccharide lipid compound is administered in a therapeutically effective amount. Furthermore, in one aspect of the methods described above, the synthetic disaccharide lipid compound is a compound of the general formula V, X or XV. In one aspect of the methods described above, the synthetic disaccharide lipid compound is a compound of the general formula V. In one aspect of the methods described above, the synthetic disaccharide lipid compound is a compound of the general formula X. In one aspect of the methods described above, the synthetic disaccharide lipid compound is a compound of the general formula XV.

In the methods disclosed herein, the subject may be a mammal. In certain embodiments, the subject is a human.

The compounds and pharmaceutical compositions can be administered in a variety of dosage ranges. In one aspect of the foregoing embodiments, the dosage of the synthetic disaccharide lipid compound is from about 0.0001 µg/kg to about 5 mg/kg. In another aspect of the foregoing embodiments, the dosage of the disaccharide synthetic lipid compound is from about 0.01 µg/kg to about 2 mg/kg. In another aspect of the foregoing embodiments, the dosage of the disaccharide synthetic lipid compound is from about 0.1 µg/kg to about 1 mg/kg. In another aspect of the foregoing embodiment, the dosage of the disaccharide synthetic lipid compound is from about 0.1 µg/kg to about 0.1 mg/kg. In another aspect of the foregoing embodiment, the dosage of the synthetic disaccharide lipid compound is from about 1 ug/kg to about 50 µg/kg. In another aspect of the foregoing embodiment, the dosage of the synthetic disaccharide lipid compound is from about 1 µg/kg to about 25 µg/kg. In another aspect of the foregoing embodiments, the dosage of the synthetic disaccharide lipid compound is from about 1 ug/kg to about 15 ug/kg. In another aspect of the foregoing embodiment, the dosage of the synthetic disaccharide lipid compound is from about 0.001 µg/kg to about 15 µg/kg. In another aspect of the foregoing embodiments, the dosage of the synthetic disaccharide lipid compound is from about 0.01 µg/kg to about 15 µg/kg. In another aspect of the foregoing embodiment the dosage of the synthetic disaccharide lipid compound is from about 0.1 µg/kg to about 15 µg/kg.

In the methods described herein, the subjects treated can be further treated with one or more additional active agents. These additional active agents may be delivered together with or separate from the synthetic disaccharide lipid compounds of the present disclosure. It will be evident to those skilled in the art that the number and frequency of administration will be dependent upon the response of the subject.

Antigen

An antigen, for use in certain embodiments described herein, may be any molecule or molecule complex that generates an immune response. In one embodiment, the molecule or molecule complex generates a weak or incomplete immune response. In one embodiment, the antigen is a target epitope to which an immune response is desired, a molecule (including a biomolecule such as a polypeptide or nucleic acid), a molecular complex (including molecular complexes that contain biomolecules), a sub-cellular fraction, cell or tissue (or a fraction of either) against which elicitation of an immune response is desired. When a polypeptide is an antigen, the polypeptide may be naturally occurring or recombinant. In one embodiment, the vaccine formulations of the present invention contains an antigen or antigenic composition capable of eliciting an immune response against a human or mammalian pathogen; in such an embodiment the antigen may be derived from such pathogen or be an antigen which cross reacts with such pathogen.

Pharmaceutical Compositions

The present disclosure provides various pharmaceutical compositions. In one embodiment, the pharmaceutical compositions of the present disclosure comprise, consist of or consist essentially of at least one synthetic disaccharide lipid compound of the present disclosure and a pharmaceutically acceptable carrier, excipient or diluent. The pharmaceutical compositions of the present disclosure may further comprise additional agents, such as, but not limited to, second adjuvants and an antigen.

In one embodiment, the pharmaceutical compositions of the present disclosure comprise, consist of or consist essentially of at least one synthetic disaccharide lipid compound of the present disclosure and a pharmaceutically acceptable carrier, excipient or diluent.

In one embodiment, the pharmaceutical compositions of the present disclosure comprise, consist of or consist essentially of at least one synthetic disaccharide lipid compound of the present disclosure, a pharmaceutically acceptable carrier, excipient or diluent and an antigen.

In another embodiment, the pharmaceutical compositions of the present disclosure comprise, consist of or consist essentially of at least one synthetic disaccharide lipid compound of the present disclosure and a pharmaceutically acceptable carrier, excipient or diluent and a second adjuvant.

In still another embodiment, the pharmaceutical compositions of the present disclosure comprise, consist of or consist essentially of at least one synthetic disaccharide synthetic lipid compound of the present disclosure, a pharmaceutically acceptable carrier, excipient or diluent, an antigen and a second adjuvant.

In one aspect of the foregoing embodiments, the at least one synthetic disaccharide lipid compound of the present disclosure is a compound of the general structure (I). In another aspect of the foregoing embodiments, the at least one synthetic disaccharide lipid compound of the present disclosure is a compound of the general structure (II). In still another aspect of the foregoing embodiments, the at least one synthetic disaccharide lipid compound of the present disclosure is a compound of the general structure (III). In yet another aspect of the foregoing embodiments, the at least one synthetic disaccharide lipid compound of the present disclosure is a compound of the general structure (IV). In a further aspect of the foregoing embodiments, the at least one synthetic disaccharide lipid compound of the present disclosure is a compound of the general structure (V). In one aspect of the foregoing embodiments, the at least one synthetic disaccharide lipid compound of the present disclosure is a compound of the general structure (VI). In another aspect of the foregoing embodiments, the at least one synthetic disaccharide lipid compound of the present disclosure is a compound of the general structure (VII). In still another aspect of the foregoing embodiments, the at least one synthetic disaccharide lipid compound of the present disclosure is a compound of the general structure (VIII). In yet another aspect of the foregoing embodiments, the at least one synthetic disaccharide lipid compound of the present disclosure is a compound of the general structure (IX). In a further aspect of the foregoing embodiments, the at least one synthetic disaccharide lipid compound of the present disclosure is a compound of the general structure (X). In one aspect of the foregoing embodiments, the at least one synthetic disaccharide lipid compound of the present disclosure is a compound of the general structure (XI). In another aspect of the foregoing embodiments, the at least one synthetic disaccharide lipid compound of the present disclosure is a compound of the general structure (XII). In still another aspect of the foregoing embodiments, the at least one synthetic disaccharide lipid compound of the present disclosure is a compound of the general structure (XIII). In yet another aspect of the foregoing embodiments, the at least one synthetic disaccharide lipid compound of the present disclosure is a compound of the general structure (XIV). In yet another aspect of the foregoing embodiments, the at least one synthetic disaccharide lipid compound of the present disclosure is a compound of the general structure (XV). In a further aspect of the foregoing embodiments, the at least one synthetic disaccharide lipid compound of the present disclosure is a compound of the general structure (XVI). In a further aspect of the foregoing embodiments, the at least one synthetic disaccharide lipid compound of the present disclosure is a compound of the general structure (XVII). In a further aspect of the foregoing embodiments, the at least one synthetic disaccharide lipid compound of the present disclosure is a compound of the general structure (XVIII). In a further aspect of the foregoing embodiments, the at least one synthetic disaccharide lipid compound of the present disclosure is a compound of the general structure (XIX). In a further aspect of the foregoing embodiments, the at least one synthetic disaccharide lipid compound of the present disclosure is a compound of the general structure (XX).

In yet a further aspect of the foregoing embodiments, the at least one synthetic disaccharide lipid compound of the present disclosure is a compound of the general structure (V), (X), (XV) or (XX). In yet a further aspect of the foregoing embodiments, the at least one synthetic disaccharide lipid compound of the present disclosure is a compound of the general structure (V). In yet a further aspect of the foregoing embodiments, the at least one synthetic disaccharide lipid compound of the present disclosure is a compound of the general structure (X). In yet a further aspect of the foregoing embodiments, the at least one synthetic disaccharide lipid compound of the present disclosure is a compound of the general structure (XV). In yet a further aspect of the foregoing embodiments, the at least one synthetic disaccharide lipid compound of the present disclosure is a compound of the general structure (XX).

In one aspect of the foregoing embodiments, the pharmaceutical composition is a vaccine composition. As set forth above, such a vaccine composition may contain only a synthetic disaccharide lipid compound of the present disclosure and a pharmaceutically acceptable carrier, excipient or diluent. As such, the immunostimulating effects will be provided by the synthetic disaccharide lipid compound. Furthermore, as set forth above, such a vaccine composition may contain only a synthetic disaccharide lipid compound of the present disclosure, a pharmaceutically acceptable carrier, excipient or diluent and an antigen. As such, the immunostimulating effects will be provided by the synthetic disaccharide lipid compound and/or the antigen. Furthermore, as set forth above, such a vaccine composition may contain only a synthetic disaccharide lipid compound of the present disclosure, a pharmaceutically acceptable carrier, excipient or diluent, an antigen and a second adjuvant. As such, the immunostimulating effects will be provided by the synthetic disaccharide lipid compound, the antigen and/or the second adjuvant.

In one aspect of the foregoing embodiments, the second adjuvant is any adjuvant known in the art. The second adjuvant is a compound or compounds that display adjuvant activity when administered to a subject (i.e., altering, increasing or decreasing, the potency and/or longevity of an immune response as described in Powell and Newman, "Vaccine design—The Subunit and Adjuvant Approach", 1995, Plenum Press, New York). Second adjuvants include, but are not limited to, saponins and saponin mimetics (such as but not limited to QS21, QS17, QS7 and mimetics), alum, plant alkaloids (such as but not limited to tomatine), detergents (such as but not limited to saponin, escin, digitonin polysorbate 80, Span 85 and stearyl tyrosine), block copolymer or biodegradable polymer (such as but not limited to Pluronic, L121, CRL1005, poly(lacetic-co-glycolic acid), poly(lacetic acid), poly-(D,L-lactide-co-glycolide) and polyinosinic:polycytidylic acid), one or more cytokines (such as but not limited to GM-CSF, IL-2, IL-7, IL-12, TNF-α, IFN-γ), and an imidazoquinoline immune response modifier (such as but not limited to resiquimod (R848), imiquimod and gardiquimod). More than one second adjuvant may be used.

In one aspect of the foregoing embodiments, the additional components of the pharmaceutical composition are fee from compounds that induce an immune response (excluding the synthetic disaccharide lipid compound, antigen and second adjuvant).

The pharmaceutical compositions disclosed may comprise one or more compounds of the present disclosure, alone or in combination with additional active agents, in combination with a pharmaceutically acceptable carrier, excipient or diluent. Examples of such carrier, excipient or diluent and methods of formulation may be found in Remington: The Science and Practice of Pharmacy (20~" Ed., Lippincott, Williams & Wilkins, Daniel Limmer, editor). Such pharmaceutical compositions may be used in the manufacture of a medicament for use in the methods of treatment and prevention described herein. The compounds of the disclosure are useful in both free form and in the form of pharmaceutically acceptable salts.

The pharmaceutically acceptable carrier, excipient or diluent described herein, are well-known to those who are skilled in the art. The choice of carrier, excipient or diluent will be determined in part by the particular compound(s), as well as by the particular method used to administer the composition. Accordingly, there is a wide variety of suitable formulations of the pharmaceutical composition of the present invention. The following methods and descriptions are merely exemplary and are in no way limiting. Suitable carriers, excipients or diluents include solvents such as water, alcohol, and propylene glycol, solid absorbants and diluents, surface active agents, suspending agent, tableting binders, lubricants, flavors, and coloring agents. The pharmaceutically acceptable carriers can include polymers and polymer matrices. Typically, the foregoing are chemically inert to the active agents in the composition and has no detrimental side effects or toxicity under the conditions of use. The compounds of the present disclosure and pharmaceutical compositions containing such compounds as described in the instant disclosure can be administered by any conventional method available for use in conjunction with pharmaceuticals, either as individual therapeutic agents or in combination with additional therapeutic agents.

In one embodiment, the compounds of the present disclosure are administered in a therapeutically effective amount, whether alone or as a part of a pharmaceutical composition. The therapeutically effective amount and the dosage administered will, of course, vary depending upon known factors, such as the pharmacodynamic characteristics of the particular agent and its mode and route of administration, the age, health and weight of the recipient; the severity and stage of the disease state or condition; the kind of concurrent treatment; the frequency of treatment; and the effect desired.

The total amount of the compound administered will also be determined by the route, timing and frequency of administration as well as the existence, nature, and extent of any adverse side effects that might accompany the administration of the compound and the desired physiological effect. It will be appreciated by one skilled in the art that various conditions or disease states, in particular chronic conditions or disease states, may require prolonged treatment involving multiple administrations.

The pharmaceutical compositions may be in any form which allows for the composition to be administered to a patient. For example, the composition may be in the form of a solid, liquid or gas (aerosol). Typical routes of administration include, without limitation, oral, topical, parenteral, sublingual and intranasal (e.g., as a spray). The term parenteral as used herein includes iontophoretic, passive transdermal and also subcutaneous injections, intravenous, intramuscular, intrasternal, intracavemous, intrathecal, intrameatal injection or infusion techniques. The pharmaceutical compositions are formulated to allow the compounds of the present disclosure contained therein to be bioavailable upon administration.

In a one embodiment, the pharmaceutical composition is a stable suspension (such as but not limited to an aqueous suspension) of less than 0.1 μm, 0.2 μm or 0.3 μm and further comprises at least one component selected from the group consisting of phospholipids, fatty acids, surfactants, detergents, saponins, fluorodated lipids, and the like. Formulations suitable for parenteral administration include aqueous and non-aqueous, isotonic sterile injection solutions, which can contain anti-oxidants, buffers, bacteriostats, and solutes that render the formulation isotonic with the blood of the patient, and aqueous and nonaqueous sterile suspensions that can include suspending agents, solubilizers, thickening agents, stabilizers, and preservatives. The compound(s) can be administered in a physiologically acceptable diluent in a pharmaceutically acceptable carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol such as poly(ethyleneglycol) 400, glycerol ketals, such as 2,2-dimethyl-1,3-dioxolane-4-methanol, ethers, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyldialkylammonium halides, and alkylpyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene polypropylene copolymers, (d) amphoteric detergents such as, for example, alkyl .beta.-aminopropionates, and 2-alkylimidazoline quaternary ammonium salts, and (e) mixtures thereof.

The parenteral formulations typically contain from about 0.5% to about 50% by weight of the compound(s) in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol.

In one embodiment, the pharmaceutical composition is formulated in a manner which can be aerosolized for delivery via nasal or pulmonary inhalation. These aerosol formulations can be placed into pressurized acceptable propellants, such as dichlorodifluoromethane, propane and nitrogen. Such aerosol formulations may be administered by metered dose inhalers. They also may be formulated as pharmaceuticals for non-pressured preparations, such as in a nebulizer or an atomizer.

The compound(s) of the present disclosure, alone or in combination with other suitable components, may be administered in an aqueous solution as a nasal or pulmonary spray and may be dispensed in spray form by a variety of methods known to those skilled in the art. Systems for dispensing liquids as a nasal spray are disclosed in U.S. Pat. No. 4,511,069. The formulations may be presented in multi-dose containers, for example in the sealed dispensing system disclosed in U.S. Pat. No. 4,511,069. Additional aerosol delivery forms may include, e.g., compressed air-, jet-, ultrasonic-, and piezoelectric nebulizers, which deliver the active agent dissolved or suspended in a pharmaceutical solvent, e.g., water, ethanol, or a mixture thereof. Nasal and pulmonary solutions of the present invention typically comprise the drug or drugs to be delivered, optionally formulated with a surface-active agent, such as a nonionic surfactant (e.g., polysorbate-80), and one or more buffers. In some embodiments of the present invention, the nasal spray solution further comprises a propellant. The pH of the nasal spray solution is optionally between about pH 3.0 and 6.0, preferably 4.5±0.5. Suitable buffers for use within these compositions are as described above or as otherwise known in the art. Other components may be added to enhance or maintain chemical stability, including preservatives, surfactants, dispersants, or gases. Suitable preservatives include, but are not limited to, phenol, methyl paraben, paraben, m-cresol, thiomersal, chlorobutanol, benzylalkonium chloride, and the like. Suitable surfactants include, but are not limited to, oleic acid, sorbitan trioleate, polysorbates, lecithin, phosphatidyl cholines, and various long chain diglycerides and phospholipids. Suitable dispersants include, but are not limited to, ethylenediaminetetraacetic acid, and the like. Suitable gases include, but are not limited to, nitrogen, helium, chlorofluorocarbons (CFCs), hydrofluorocarbons (HFCs), carbon dioxide, air, and the like.

Within alternate embodiments, nasal and pulmonary formulations are administered as dry powder formulations comprising the active agent in a dry, usually lyophilized, form of an appropriate particle size, or within an appropriate particle size range, for intranasal delivery. Minimum particle size appropriate for deposition within the nasal or pulmonary passages is often about 0.5 μm mass median equivalent aerodynamic diameter (MMEAD), commonly about 1 μm MMEAD, and more typically about 2 μm MMEAD. Maximum particle size appropriate for deposition within the nasal passages is often about 10 μm MMEAD, commonly about 8 μm MMEAD, and more typically about 4 μm MMEAD. Intranasally and pulmonaryly respirable powders within these size ranges can be produced by a variety of conventional techniques, such as jet milling, spray drying, solvent precipitation, supercritical fluid condensation, and the like. These dry powders of appropriate MMEAD can be administered to a patient via a conventional dry powder inhaler (DPI), which relies on the patient's breath, upon pulmonary or nasal inhalation, to disperse the power into an aerosolized amount. Alternatively, the dry powder may be administered via air-assisted devices that use an external power source to disperse the powder into an aerosolized amount, e.g., a piston pump.

To formulate compositions for nasal or pulmonary delivery, the active agent can be combined with various pharmaceutically acceptable additives, as well as a base or carrier for dispersion of the active agent(s). Desired additives include, but are not limited to, pH control agents, such as arginine, sodium hydroxide, glycine, hydrochloric acid, citric acid, etc.

In addition, local anesthetics (e.g., benzyl alcohol), isotonizing agents (e.g., sodium chloride, mannitol, sorbitol), adsorption inhibitors (e.g., Tween SO), solubility enhancing agents (e.g., cyclodextrins and derivatives thereof), stabilizers (e.g., serum albumin), and reducing agents (e.g., glutathione) can be included. When the composition for nasal or pulmonary delivery is a liquid, the tonicity of the formulation, as measured with reference to the tonicity of 0.9% (w/v) physiological saline solution taken as unity, is typically adjusted to a value at which no substantial, irreversible tissue damage will be induced in the nasal mucosa at the site of administration. Generally, the tonicity of the solution is adjusted to a value of about ⅓ to 3, more typically ½ to 2, and most often ¾ to 1.7.

In one embodiment, a pharmaceutical composition of the disclosure is an emulsion. Single or multiphase emulsion systems are known in the art and may be used. Oil in water emulsion adjuvants and water in oil emulsions may be used. In one embodiment, a pharmaceutical composition of the disclosure is an emulsion of oil in water wherein the synthetic disaccharide lipid compound is incorporated in the oil phase. The oil may be any vegetable oil, fish oil, animal oil or synthetic oil, which is not toxic to the subject and is capable of being transformed by metabolism. Nuts (such as peanut oil), seeds, and grains are common sources of vegetable oils. Squalene is an unsaturated oil which is found in large quantities in shark-liver oil, and in lower quantities in olive oil, wheat germ nil, rice bran oil, and yeast. In one embodiment, the oil in water emulsions are squalene in water emulsions. Such emulsions may contain additional components such as a second adjuvant and other compounds such as antioxidants and other lipid compounds to stabilize the emulsion. The size of the oil droplets found within the stable oil in water emulsion are preferably less than 1 μm, such as in the range of 25 to 500 nm. The methods of producing oil in water emulsions are well known.

The compounds and compositions of the present disclosure can be presented in unit-dose or multi-dose sealed containers, such as ampules and vials, requiring only the addition of the sterile liquid excipient, for example, water for injections, immediately prior to use. Certain compositions can be stored in a freeze-dried (lyophilized) condition if desired. Extemporaneous injection solutions and suspensions can be prepared from sterile powders, granules, and tablets. The requirements for effective pharmaceutically acceptable carriers for injectable compositions are well known to those of ordinary skill in the art. See Pharmaceutical and Pharmacy Practice, J.B. Lippincott Co., Philadelphia, Pa., Banker and Chalmers, Eds., 238-250 (1982) and ASHP Handbook on Injectable Drugs, Toissel, 4th ed., 622-630 (1986).

In one embodiment, the pharmaceutical composition is in the form of a liposome or other slow release mechanism. Suitable slow release mechanisms are described in U.S. Pat. No. 5,888,519 (which is hereby incorporated by reference for such teaching) and include polymers of various types, microcapsules, and microspheres.

Preferred methods for making liposome preparations are described by Bangham (Bangham et. al., 1965). This preparation involves dissolving phospholipids in an organic solvent which is then evaporated to dryness leaving a thin lipid film on the inside of the test tube. The dry lipid film is then hydrated in an appropriate amount of aqueous phase and the mixture is heated to above the phase transition temperature of the lipids and allowed to "swell". The resulting liposomes which consist of multilamellar vesicles (MLV's) are dispersed by shaking the test tube. The lipids constituting the vesicular bilayer membranes are organized such that the hydrophobic hydrocarbon "tails" are oriented toward the center of the bilayer while the hydrophilic "heads" orient towards the in- and outside aqueous phase, respectively. This preparation provides the basis for producing unilamellar vesicles (UV) by methods such as sonication (Papahadjopoulos et. al., 1967) or extrusion as described by Cullis et. al. in U.S. Pat. No. 5,008,050 (each of the foregoing are hereby incorporated by reference for such teaching).

Liposomes are ordinarily understood to consist of lipid membranes that are capable of enclosing an internal aqueous space and the membranes may consist of a variety of types of lipids. For clarity, the term liposome should not be construed to require the presence of a closed membrane, rather the term should be understood to require that the lipids self-associate such that they form a particulate structure. Among the lipids that have been used either alone or in combination with other lipids to construct liposomes are included phospholipids, glycolipids, glycophospholipids, diglycerides, triglycerides, sterols, steroids, terpenoids, free fatty acids, and lipoidal vitamins.

Release of materials from liposomes most commonly occurs by diffusion but a number of other release mechanisms may also apply. Furthermore, the liposome may act solely as a carrier rather than as a drug release reservoir. The result is a slow release of the compound from the liposome. These mechanisms are described in further detail by in Langer, R., New methods of drug delivery. Science 249:1527-1533 (1990). In a particular embodiment, liposomes for use in the pharmaceutical formulations of the present disclosure comprise a mixture of dimyristoyl phosphatidylcholine (DMPC), dimyristoyl phosphatidylglycerol (DMPG), and cholesterol (Chol) In a particular embodiment, the DMPC/DMPG/Chol are present in molar ratios of 9/1/7. In another particular embodiment, the DMPC/DMPG/Chol are present in molar ratios of 1.8/0.2/1.5. The compounds of the present disclosure may be incorporated into such liposomes as is known in the art (see for example, PCT publication numbers WO2007/068411 and WO2005/081872 which are hereby incorporated by reference herein for such teachings) and described herein.

EXAMPLES

Example 1

Purity of Synthetic Disaccharide Lipid Compounds

Synthetic disaccharide lipid compounds of the present disclosure were synthesized and characterized. The compounds synthesized include compounds of the general structural formula V (sometimes referred to as MPLA-B), X (sometimes referred to as MPLA-D) and XVI (sometimes referred to as MPLA-C).

Purity of MPLA-B

MPLA-B has the structure shown below (as well as in general structural formula V). The molecular weight of this compound is 1537.11 ($C_2H_{158}N_3O_{20}P$).

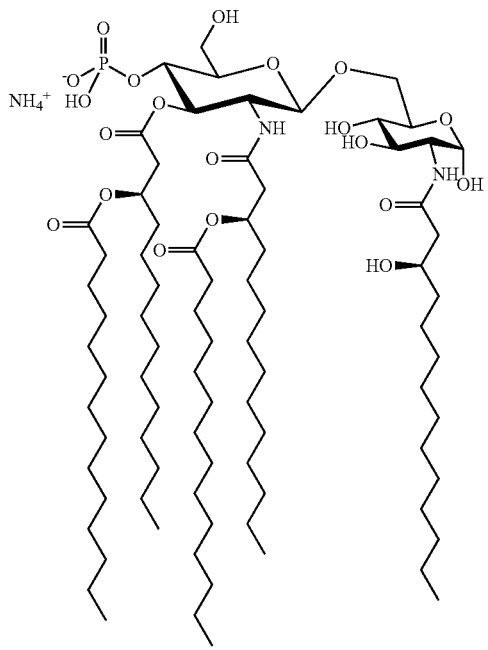
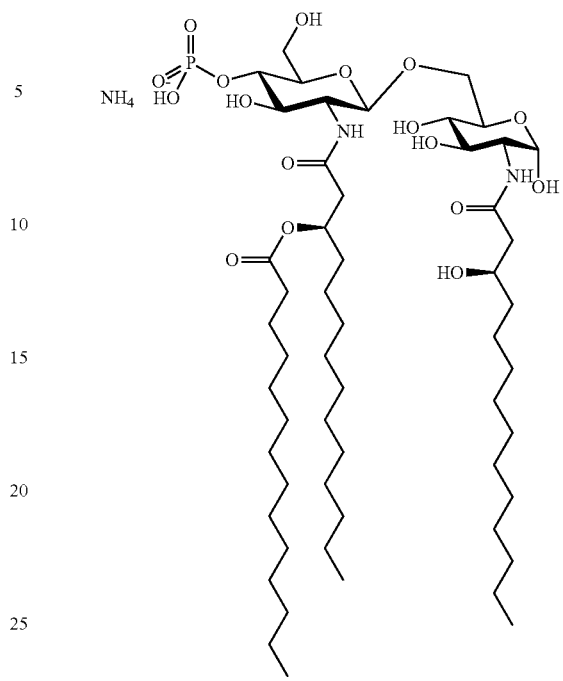

In this compound, acyl chains are present at the 2, 2' and 3' positions, with 2 acyl chains being present at the 2' and 3' positions. Each acyl chain has a chain length of 14 carbons and each acyl chain is saturated.

The compound was analyzed by TLC, phosphorous NMR, proton NMR and mass spectroscopy. The results are shown in Table 1A below. As can be seen the compound was determined to be over 99% pure and to have a structure consistent with the structure shown above.

In this compound, acyl chains are present at the 2 and 2', with 2 acyl chains being present at the 2' and one acyl chain being present at the 2 position. Each acyl chain has a chain length of 14 carbons and each acyl chain is saturated.

The compound was analyzed by TLC, phosphorous NMR, proton NMR and mass spectroscopy. The results are shown in Table 1B below. As can be seen the compound was determined to be over 99% pure and to have a structure consistent with the structure shown above.

TABLE 1A

| Test | Limits | Results |
|---|---|---|
| TLC | >99% purity | >99% purity |
| Ninhydrin | Negative | Negative |
| Phosphorous | Positive | Positive |
| Iodine | One spot | One spot |
| Charcoal | Positive | Positive |
| Phosphorus NMR | Consistent with structure, 1 phosphorus containing peak | Pass |
| Proton NMR | Consistent with structure | Pass |
| Mass Spectroscopy | $[M-NH_4]^- = 1518.11 \pm 1$ amu | $[M-NH_4]^- = 1518.40$ amu |

TABLE 1B

| Test | Limits | Results |
|---|---|---|
| TLC | >99% purity | >99% purity |
| Ninhydrin | Negative | Negative |
| Phosphorous | Positive | Positive |
| Iodine | One spot | One spot |
| Charcoal | Positive | Positive |
| Proton NMR | Consistent with structure | Pass |
| Mass Spectroscopy | $[M-NH_4]^- = 1082.4 \pm 1$ amu | $[M-NH_4]^- = 1082.4$ amu |

Purity of MPLA-D

MPLA-D has the structure shown below (as well as in general structural formula X). The molecular weight of this compound is 1100.40 ($C_{54}H_{106}N_3O_{17}P$).

Purity of MPLA-C

MPLA-C has the structure shown below (as well as in general structural formula XV). The molecular weight of this compound is 1326.76 ($C_6H_{132}N_3O_{19}P$).

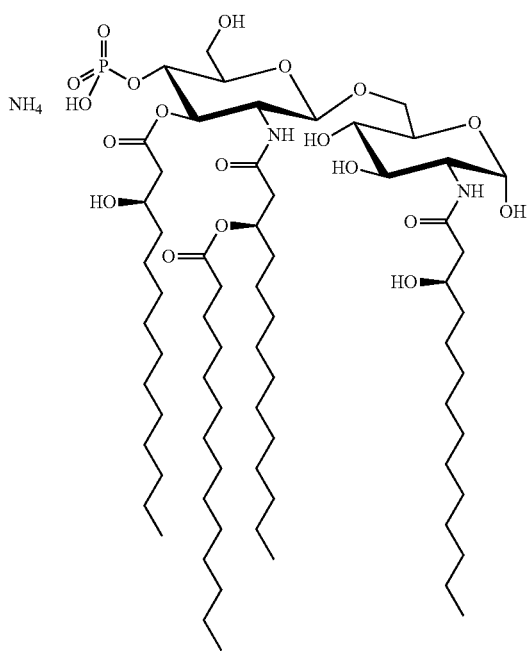

In this compound, acyl chains are present at the 2, 2' and 3' positions, with 2 acyl chains being present at the 2' and one acyl chain being present at the 3' and 2 positions. Each acyl chain has a chain length of 14 carbons and each acyl chain is saturated.

The compound was analyzed by TLC, phosphorous NMR, proton NMR and mass spectroscopy. The results are shown in Table 1C below. As can be seen the compound was determined to be over 99% pure and to have a structure consistent with the structure shown above.

TABLE 1C

| Test | Limits | Results |
| --- | --- | --- |
| TLC | >99% purity | >99% purity |
| Ninhydrin | Negative | Negative |
| Phosphorous | Positive | Positive |
| Iodine | One spot | One spot |
| Charcoal | Positive | Positive |
| Proton NMR | Consistent with structure | Pass |
| Mass Spectroscopy | $[M-NH4]^- = 1308.76 \pm 1$ amu | $[M-NH4]^- = 1305.5$ amu |

Example 2

Synthetic Disaccharide Lipid Compounds Stimulate the Human and Mouse TLR-4 Receptor In this example, the ability of the synthetic disaccharide lipid compounds of the present disclosure was tested for their ability to activate the human and mouse Toll-like receptor 4 (TLR-4). TLR-4 detects lipopolysaccharide (LPS) found in most gram-negative bacteria and is thus important in the activation of the innate immune system. TLR-4 has also been designated as CD284. TLR-4 signals the presence of LPS by associating with two other cell-surface proteins, LY96 (or MD2) and CD14, and when the TLR-4:LY96:CD14 complex binds LPS the intracellular NFκB signaling pathaway is activated. Mutations in the TLR4 gene have been associated with differences in LPS responsiveness. The results show that the synthetic disaccharide lipid compounds of the present disclosure were effective in stimulating both the human and mouse TLR-4 receptor.

HEK-293 cell lines engineered to functionally over-express human or murine TLR-4 receptor were utilized in the experiments below. These cells also contain a reporter gene (a secreted alkaline phosphatase) under the control of a NFκB inducible promoter. TLR-4 activation results are given as optical density (OD) values after 18 hours stimulation of the designated HEK-293 cell lines.

Samples and controls are tested in duplicate on recombinant HEK-293 cell lines. The negative controls for the assay were the parental HEK-293 cell lines transfected only with the reporter gene. Negative control cells were stimulated with TNF-α, an inducer of NFκB activity. The positive controls for the assay were HEK-293 cells transfected with human TLR-4 (hTLR-4) or mouse TLR-4 (mTLR-4) along with the reporter construct and activated with LPS 0111 (obtained from *E. coli* 0111:B4strain) from 100 ng/ml to 0.3 ng/ml or with LPS K12 (obtained from *E. coli* K12 strain) from 100 ng/ml to 0.03 ng/ml.

The synthetic disaccharide lipid compound used in this assay was that compound of the structure V (referred to herein as MPLA-B). As a comparison, results are also presented using the hexa-acyl disaccharide lipid compound known as PHAD™ (Avanti Polar Lipids, Alabaster, Ala.; also referred to herein as MPLA-A). PHAD™ has been shown to have immunostimulatory properties. Test compounds were used at concentrations of 10 μg/ml (corresponding to 5.7 μM for PHAD™ and to 6.5 μM for MPLA-B) to 0.01 μg/ml when tested alone or at 5 μg/ml to 0.005 μg/ml each when tested in combination.

The results are presented in Tables 2-10. Tables 2 and 3 show the negative control results for the hTLR-4 cells indicating that neither of the test compounds, alone or in combination, stimulated the reporter construct in the absence of hTLR-4.

TABLE 2

| | 100 ng/ml | 30 ng/ml | 10 ng/ml | 3 ng/ml | 1 ng/ml | 0.3 ng/ml |
| --- | --- | --- | --- | --- | --- | --- |
| TNF-α | 0.477 | 0.470 | 0.047 | 0.005 | 0.009 | 0.004 |

| | 10 μg/ml | 1 μg/ml | 0.3 μg/ml | 0.1 μg/ml | 0.03 μg/ml | 0.01 μg/ml |
| --- | --- | --- | --- | --- | --- | --- |
| MPLA-B | −0.015 | 0.005 | 0.019 | 0.011 | 0.003 | 0.031 |
| PHAD™ | −0.009 | −0.026 | 0.015 | −0.013 | −0.003 | 0.003 |

TABLE 3

| | 100 ng/ml | 30 ng/ml | 10 ng/ml | 3 ng/ml | 1 ng/ml | 0.3 ng/ml |
| --- | --- | --- | --- | --- | --- | --- |
| TNF-α | 0.477 | 0.470 | 0.047 | 0.005 | 0.009 | 0.004 |

| | 5 μg/ml | 0.5 μg/ml | 0.15 μg/ml | 0.05 μg/ml | 0.015 μg/ml | 0.005 μg/ml |
| --- | --- | --- | --- | --- | --- | --- |

TABLE 3-continued

| | | | | | | |
|---|---|---|---|---|---|---|
| MPLA-B + PHAD ™ | 0.002 | −0.003 | 0.011 | 0.001 | 0.002 | 0.021 |

Tables 4 and 5 show that the test compounds, both alone and in combination, stimulated the hTLR-4 receptor.

TABLE 4

| | 30 ng/ml | 10 ng/ml | 3 ng/ml | 1 ng/ml | 0.3 ng/ml | 0.1 ng/ml |
|---|---|---|---|---|---|---|
| LPS 0111 | 1.387 | 1.262 | 1.135 | 0.899 | 0.577 | 0.275 |

TABLE 4-continued

| | 10 µg/ml | 1 µg/ml | 0.3 µg/ml | 0.1 µg/ml | 0.03 µg/ml | 0.01 µg/ml |
|---|---|---|---|---|---|---|
| MPLA-B | 1.169 | 0.835 | 0.697 | 0.510 | 0.102 | −0.017 |
| PHAD ™ | 1.539 | 1.347 | 1.187 | 1.191 | 0.071 | 0.033 |

TABLE 5

| | 30 ng/ml | 10 ng/ml | 3 ng/ml | 1 ng/ml | 0.3 ng/ml | 0.1 ng/ml |
|---|---|---|---|---|---|---|
| TNF-α | 1.387 | 1.262 | 1.135 | 0.899 | 0.577 | 0.275 |

| | 5 µg/ml | 0.5 µg/ml | 0.15 µg/ml | 0.05 µg/ml | 0.015 µg/ml | 0.005 µg/ml |
|---|---|---|---|---|---|---|
| MPLA-B + PHAD ™ | 1.487 | 1.332 | 1.234 | 0.866 | −0.002 | 0.014 |

Tables 6 and 7 show the negative control results for the mTLR-4 cells indicating that neither of the test compounds, alone or in combination, stimulated the reporter construct in the absence of mTLR-4.

TABLE 6

| | 100 ng/ml | 30 ng/ml | 10 ng/ml | 3 ng/ml | 1 ng/ml | 0.3 ng/ml |
|---|---|---|---|---|---|---|
| TNF-α | 3.935 | 3.586 | 1.233 | 0.033 | 0.017 | 0.035 |

| | 10 µg/ml | 1 µg/ml | 0.3 µg/ml | 0.1 µg/ml | 0.03 µg/ml | 0.01 µg/ml |
|---|---|---|---|---|---|---|
| MPLA-B | −0.004 | −0.016 | 0.007 | −0.009 | 0.000 | 0.165 |
| PHAD ™ | −0.021 | −0.010 | 0.001 | −0.019 | 0.010 | 0.024 |

TABLE 7

| | 100 ng/ml | 30 ng/ml | 10 ng/ml | 3 ng/ml | 1 ng/ml | 0.3 ng/ml |
|---|---|---|---|---|---|---|
| LPS 0111 | 3.935 | 3.586 | 1.233 | 0.033 | 0.017 | 0.035 |

| | 5 µg/ml | 0.5 µg/ml | 0.15 µg/ml | 0.05 µg/ml | 0.015 µg/ml | 0.005 µg/ml |
|---|---|---|---|---|---|---|
| MPLA-B + PHAD ™ | −0.012 | 0.003 | 0.003 | −0.023 | −0.001 | 0.016 |

Tables 8 and 9 show that the test compounds, both alone and in combination stimulated the mTLR-4 receptor.

TABLE 8

|  | 30 ng/ml | 10 ng/ml | 3 ng/ml | 1 ng/ml | 0.3 ng/ml | 0.1 ng/ml |
|---|---|---|---|---|---|---|
| LPS 0111 | 3.470 | 3.473 | 3.382 | 3.106 | 2.578 | 1.795 |

|  | 10 μg/ml | 1 μg/ml | 0.3 μg/ml | 0.1 μg/ml | 0.03 μg/ml | 0.01 μg/ml |
|---|---|---|---|---|---|---|
| MPLA-B | 3.179 | 2.667 | 2.450 | 2.267 | 1.552 | 0.065 |
| PHAD ™ | 3.490 | 3.308 | 3.164 | 3.171 | 0.869 | 0.373 |

TABLE 9

|  | 30 ng/ml | 10 ng/ml | 3 ng/ml | 1 ng/ml | 0.3 ng/ml | 0.1 ng/ml |
|---|---|---|---|---|---|---|
| LPS 0111 | 1.387 | 1.262 | 1.135 | 0.899 | 0.577 | 0.275 |

|  | 5 μg/ml | 0.5 μg/ml | 0.15 μg/ml | 0.05 μg/ml | 0.015 μg/ml | 0.005 μg/ml |
|---|---|---|---|---|---|---|
| MPLA-B + PHAD ™ | 3.416 | 3.129 | 2.993 | 2.627 | 0.449 | 0.155 |

Another synthetic disaccharide lipid compound used in this assay in an independent experiment, was the compound of the structure X (referred to herein as MPLA-D). As a comparison, results are also presented using the hexa-acyl disaccharide lipid compound known as PHAD™ (Avanti Polar Lipids, Alabaster, Ala.; also referred to herein as MPLA-A). PHAD™ has been shown to have immunostimulatory properties. Test compounds were used at the following concentrations: 5.7 μM/570 nM/171 nM/57 nM/17 nM/5.7 nM/well to stimulate in duplicate mTLR4 expressing cell lines The results are presented in Table 10. Table 10 shows that MPLA-D activates the mTLR4 expressing cell line up to 570 nM.

TABLE 10

|  | 10 ng/ml | 3 ng/ml | 1 ng/ml | 0.3 ng/ml | 0.1 ng/ml | 0.03 ng/ml | 0.01 ng/ml |
|---|---|---|---|---|---|---|---|
| LPS K12 | 3.108 | 2.709 | 1.878 | 0.984 | 0.485 | 0.101 | −0.065 |

|  | 5.7 μM | 570 nM | 171 nM | 57 nM | 17 nM | 5.7 nM |
|---|---|---|---|---|---|---|
| MPLA-D | 2.541 | 0.880 | 0.251 | 0.073 | −0.004 | 0.003 |
| PHAD ™ | 3.884 | 3.917 | 3.756 | 3.703 | 3.640 | 3.368 |

The results show that the synthetic disaccharide compounds of the present disclosure are effective in activating both human and murine TLR-4.

Example 3

Synthetic Disaccharide Lipid Compounds Stimulate Splenocyte and B-Cell Proliferation In Vitro In this example, the ability of the synthetic disaccharide lipid compounds of the present disclosure were tested for their ability to stimulate the proliferation of splenocytes and B-cells in vitro. The synthetic disaccharide lipid compound used in this assay was that compound of the structure V (referred to herein as MPLA-B). As a comparison, results are also presented using the hexa-acyl disaccharide lipid compound known as PHAD™ (Avanti Polar Lipids, Alabaster, Ala.; also referred to herein as MPLA-A). PHAD™ has been shown to have immunostimulatory properties.

PHAD and MPLA-B were provided in powder form and were solubilized in DMSO at 5 mg/ml, then diluted with sterile pyrogen-free distilled water for a stock solution concentration of 500 μg/ml. These stock solutions were further diluted in RPMI complete media to make working solutions at 300 μg/ml, 100 μg/ml, and 30 μg/ml, which were then diluted into the appropriate cell culture well at a 1:100 dilution for final test concentrations of 3, 1, and 0.3 μg/ml; for the combination of MPLA-A and MPLA-B, the 300 μg/ml working stock solutions were both diluted into the appropriate cell culture well at a 1:200 dilution for final test concentrations of 1.5 μg/ml each. As a solvent control, 10% DMSO (in sterile pyrogen-free distilled water) was diluted in RPMI complete media to achieve a concentration of 6% DMSO, which was then diluted into the appropriate cell culture well at 1:100 for a final concentration of 0.06% DMSO.

Spleens from 6 C57/BL6 mice were collected and each spleen was mechanically dissociated into a single cell suspension with a 70 μm cell strainer. Each single cell suspension of splenocytes was then diluted in complete media (RPMI+10% heat-inactivated FBS, 2 mM L-glutamine, 100 U of penicillin/mL, 100 μg of streptomycin/mL and 50 μM 2-Mercaptoethanol), and manual counts of nucleated viable cells (i.e. all cells except red blood cells) were performed. The splenocytes from 3 mice were used as for the isolation of B cells as described below.

B cells were isolated from the splenocytes of 3 mice using EasySep™ Mouse B cell Enrichment Kit (STEMCELL Technologies, Catalog 19754A, Lot 11K41946) according to the manufacturer's instructions. To determine the purity after cell separation, cells were stained with antibodies against CD45 (hematopoietic marker; BD Bioscience, Catalog 553080, Lot 49362) and CD19 (B cell marker; eBioscience, Catalog 1209382, Lot E01113-1620), and analyzed by flow cytometry (Accuri® C6 Flow Cytometer) for percentage of CD45+/CD19+.

For analysis of proliferation, splenocytes and B cells grown in the presence of PHAD and MPLA, both alone and in combination, or solvent control were incubated at 37° C., 5% CO2. After 48 hours, detection and quantitation of cell proliferation was measured using a Cell Proliferation ELISA, BrdU (Roche Diagnostics, Catalog 11 647 229 001, Lot 13073200) as per the manufacturer's instructions, utilizing an M5 SpectraMax plate reader (Molecular Devices, Sunnyvale, Calif.). After incubation with BrdU, the cell plates were centrifuged to pellet the cells (plate 1), and the supernatants removed to a fresh plate (plate 2) that was also centrifuged to pellet any remaining floating cells (supernatants from plate 1 were transferred to a fresh plate and frozen at −20° C.). Cell plates 1 and 2 were then used in the proliferation assay to determine the amount of proliferation, as indicated by the absorbance (OD) of each well. The OD values of each sample were adjusted for non-specific binding by subtracting the OD values of the background control wells; OD values from plate 1 and 2 were then added together to give the total proliferation index for each sample. For samples with adjusted OD values falling below 0.05 were set at 0.05 in FIGS. 2A and 2B.

For analysis of viability, splenocytes and B cells grown in the presence of PHAD™ and MPLA, both alone and in combination, or solvent control were incubated at 37° C., 5% $CO_2$. After a 72 hour incubation, the cell plates were centrifuged to pellet any floating cells and the supernatants were removed to a fresh plate and centrifuged again to pellet any remaining cells: the supernatants were removed and frozen at −20° C. for subsequent IgM/IgG evaluation (see below), while the cell pellets from the two plates were combined and subjected to viability assessment using Cell-Titer Glo (Promega, Catalog G7571/2/3, Lot 9218) as per the manufacturer's instructions.

For the cell proliferation and viability assays, cells were seeded in flat-bottomed 96-well tissue culture-treated plates (Corning® Costar® 3595). Splenocytes were plated at a density of $1 \times 10^5$ cells/well for the proliferation assay (2 wells/condition) and $1 \times 10^6$ cells/well for the viability assay (1 well/condition); B cells were plated at $1 \times 10^5$ cells/well for both assays (2 wells/condition). Each well contained a final volume of 250 µL. Cell cultures were monitored on a daily basis for changes in the culture morphology or in the media (e.g., yellowing of the media).

Figure 1B:
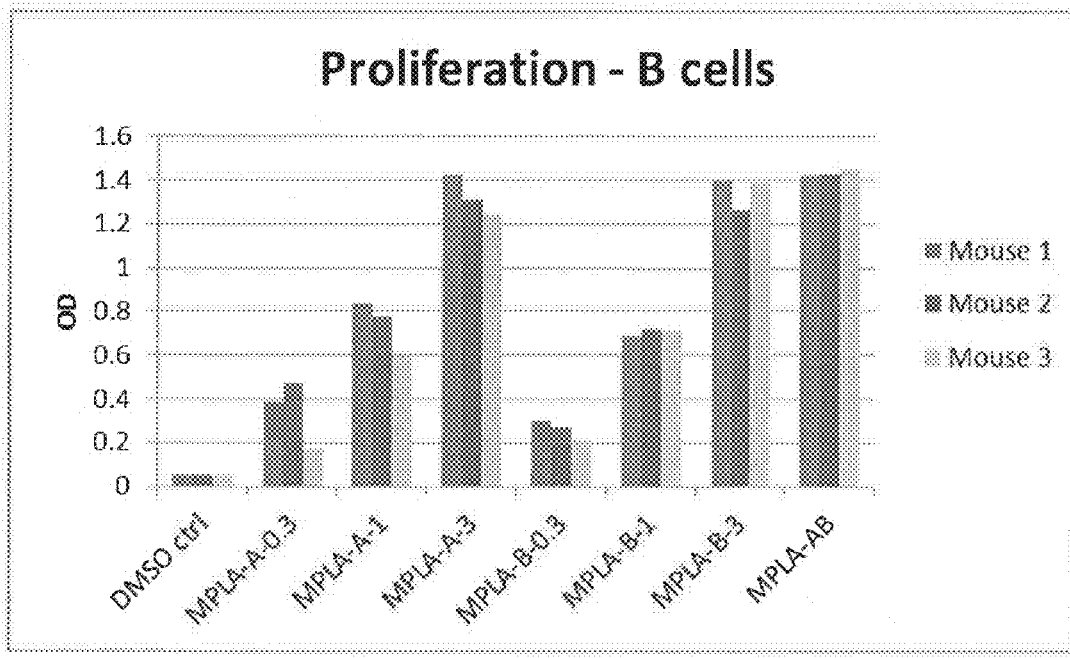
FIG. 1B shows the effect of the synthetic disaccharide lipid compounds of the present disclosure on proliferation of B cells in vitro.

As shown in FIGS. 1A and 1B, PHAD™ and MPLA-B, both alone and in combination, stimulated the proliferation of splenocytes and B cells in vitro. Splenocytes and B cells were incubated with PHAD™ and MPLA-B, both alone and in combination, or solvent as a control to examine induction of cell proliferation. After a 48 hour incubation, quantitation of cell proliferation was measured using a colorimetric immunoassay based on the measurement of BrdU incorporation into proliferating cells. FIGS. 1A and 1B shows the proliferation of splenocytes and B cells for each test condition based on the incorporation of BrdU. Both PHAD™ and MPLA-B induced proliferation in a dose-dependent manner in splenocytes (FIG. 1A) and in B cells (FIG. 1B), with slightly higher proliferation levels observed in the B cell cultures. The combination of PHAD™ and MPLA-B (1.5 µg/ml of each; total of 3 µg/ml) induced similar levels of proliferation as PHAD™ (3 µg/ml) and MPLA-B (3 µg/ml).

Figure 2A:
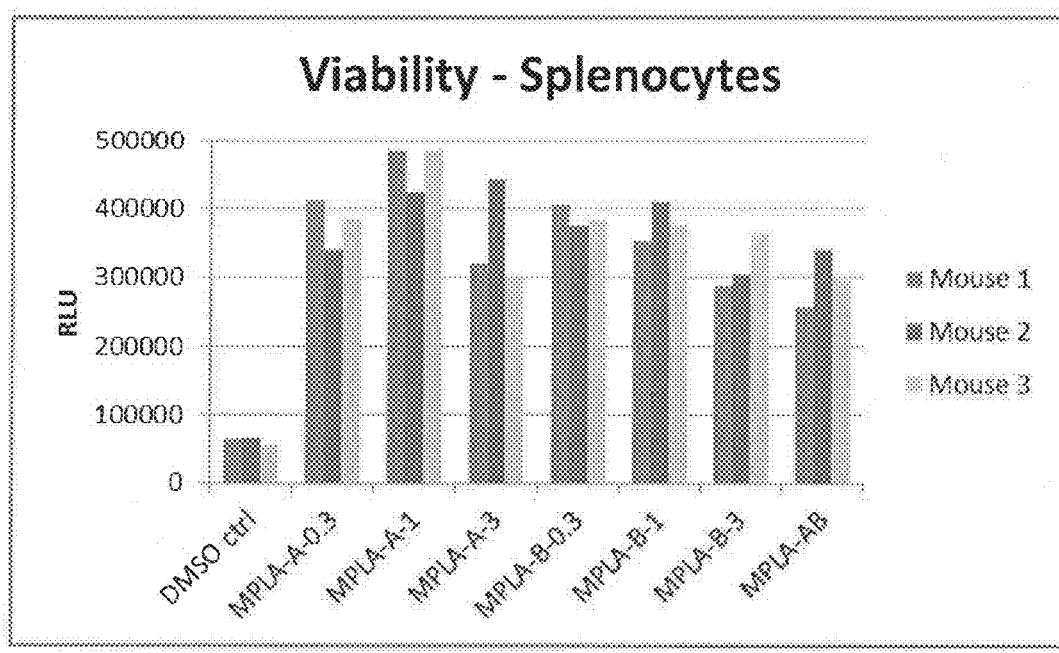
FIG. 2A shows the effect of the synthetic disaccharide lipid compounds of the present disclosure on the viability of splenocytes in vitro.
Figure 2B:
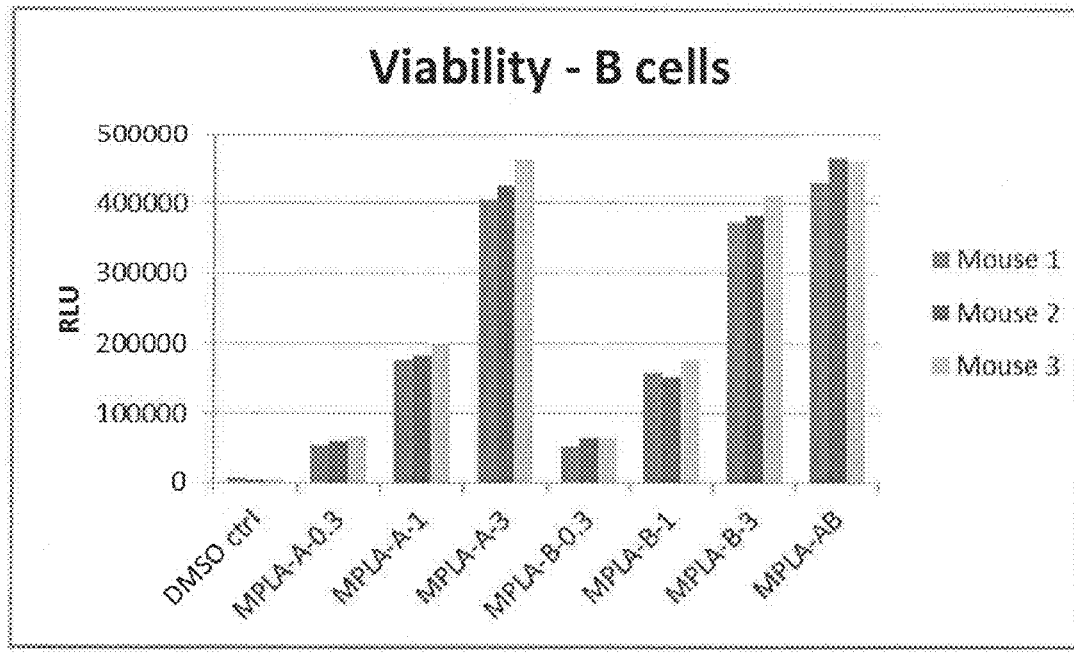
FIG. 2B shows the effect of the synthetic disaccharide lipid compounds of the present disclosure on viability of B cells in vitro.

As shown in FIGS. 2A and 2B, PHAD™ and MPLA-B, both alone and in combination, had no detrimental impact on viability of splenocytes or B cells. In fact, PHAD™ and MPLA-B, both alone and in combination, increased the viability of the tested splenocytes and B cells. Splenocytes and B cells were incubated with PHAD™ and MPLA-B, both alone and in combination, or solvent as a control. After a 72 hour incubation, supernatants were harvested for IgM/IgG determination (see below), and the viability of the remaining cells was determined using Cell Titer Glo. FIG. 2A and FIG. 2B show the viability of splenocytes and B cells, respectively, for each test condition. Splenocytes treated with PHAD™ and MPLA-B alone showed similar increased levels of viability when compared to the control; cultures treated with the combination of PHAD™ and MPLA-B (1.5 µg/ml of each; total of 3 µg/ml) induced similar viability levels as PHAD™ (3 µg/ml) and MPLA-B (3 µg/ml) (FIG. 2A). In contrast, B cell cultures treated with PHAD™ and MPLA-B showed a dose-dependent increase in viability when compared to the control; cultures treated with the combination of PHAD™ and MPLA-B (1.5 µg/ml of each; total of 3 µg/ml) demonstrated similar viability levels as PHAD™ (3 µg/ml) and MPLA-B (3 µg/ml) (FIG. 2B).

Example 4

Synthetic Disaccharide Lipid Compounds Stimulate IgM and IgG Secretion from Splenocytes and B-Cells In Vitro In this example, the ability of the synthetic disaccharide lipid compounds of the present disclosure were tested for their ability to stimulate IgM and IgG secretion from of splenocytes and B-cells in vitro. The synthetic disaccharide lipid compound used in this assay was that compound of the structure V (referred to herein as MPLA-B). As a comparison, results are also presented using the hexa-acyl disaccharide lipid compound known as PHAD™ (Avanti Polar Lipids, Alabaster, Ala.; also referred to herein as MPLA-A). PHAD™ has been shown to have immunostimulatory properties.

Materials and the conditions for splenocytes and B cell cultures are as described in Example 2. Splenocytes were plated at a density of $1 \times 10^6$ cells/well for the proliferation assay (1 wells/condition) and B cells were plated at $1 \times 10^5$ cells/well (2 wells/condition).

For assessment of IgM and IgG secretion, splenocytes and B cells grown in the presence of PHAD™ and MPLA-B, both alone and in combination, or diluent were incubated at 37° C., 5% $CO_2$. After a 72 hour incubation, the cell plates were centrifuged to pellet any floating cells and the supernatants were removed to a fresh plate and centrifuged again to pellet any remaining cells. The supernatants were removed and frozen at −20° C. ELISAs for IgM (Mouse IgM ELISA Quantitation Set, Bethyl Laboratories, Catalog E90-101, Lot E90-101-25) and IgG (Mouse IgG ELISA Quantitation Set, Bethyl Laboratories, Catalog E90-131, Lot E90-131-29) were performed as per manufacturer's instructions. All supernatant samples were diluted prior to ELISA at 1:2, 1:10, and 1:50. For determination of immunoglobulin concentrations, only those samples with OD values that fell between the range of 90-10% of the average OD of the highest concentration of the standard curve were considered as acceptable and used to determine immunoglobulin concentrations, while the value of 10% was considered as the limit of quantification (LOQ) of the assay. For each test condition, all acceptable data points were averaged, and the standard deviation was determined, where possible. If concentration values were unable to be determined, the concentration values are reported as less than the concentration value corresponding to LOQ multiplied by the lowest dilution used in the assay. For calculations and presentation in graphs, the LOQ multiplied by the lowest dilution was used.

Figure 3A:
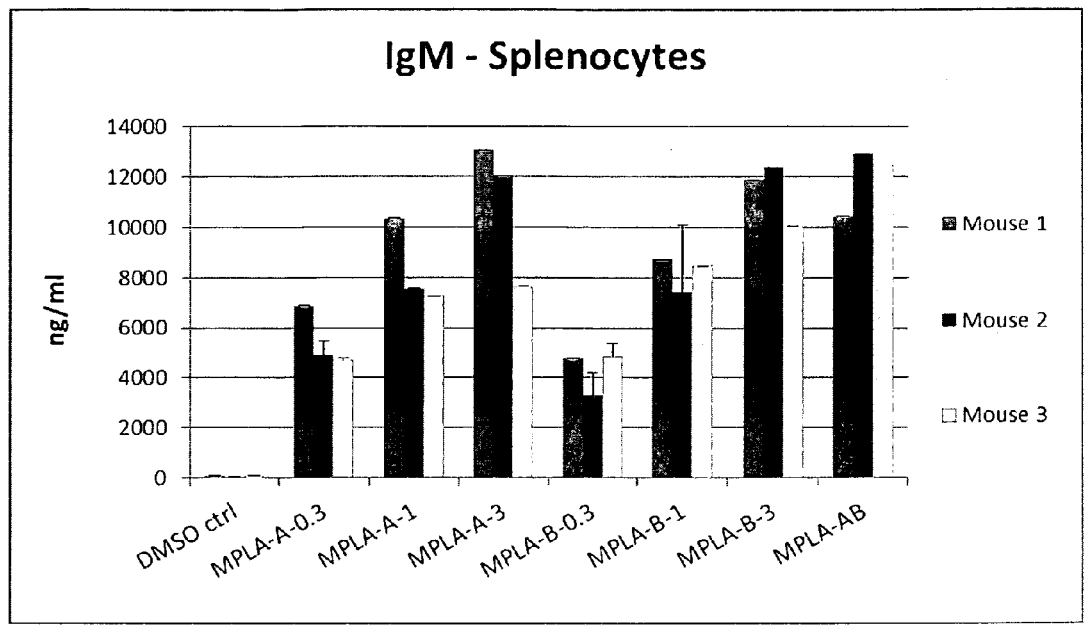
FIG. 3A shows the effect of the synthetic disaccharide lipid compounds of the present disclosure on IgM secretion from splenocytes in vitro.
Figure 3B:
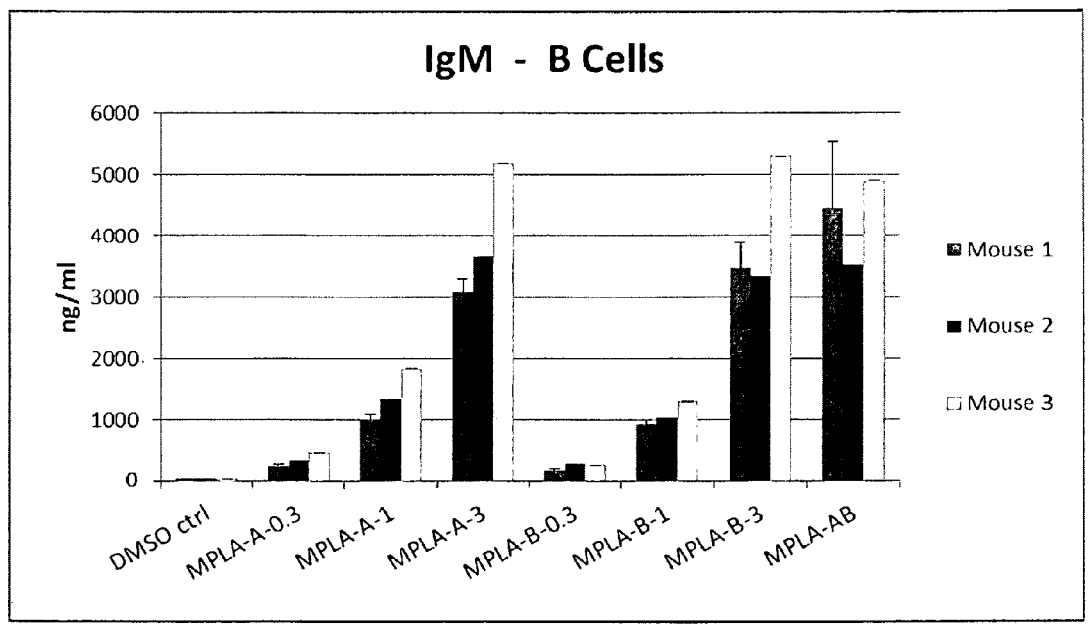
FIG. 3B shows the effect of the synthetic disaccharide lipid compounds of the present disclosure on IgM secretion from B cells in vitro.

Splenocytes and B cells were incubated with PHAD™ and MPLA-B, both alone and in combination, or solvent as a control to examine effects on secretion of IgM. After 72 hours of incubation, supernatants were harvested for IgM determination. IgM levels, as quantitated by ELISA, are shown in FIGS. 3A and 3B for splenocytes and B cells, respectively. In general, PHAD™ and MPLA-B both induced IgM production in a dose-dependent manner in splenocytes (FIG. 3A) and in B cells (FIG. 3B), with overall higher IgM levels observed in the splenocyte cultures. The combination of PHAD™ and MPLA-B (1.5 µg/ml of each; total of 3 µg/ml) induced similar levels of IgM as MPLA-A (3 µg/ml) and MPLA-B (3 µg/ml).

Figure 4A:
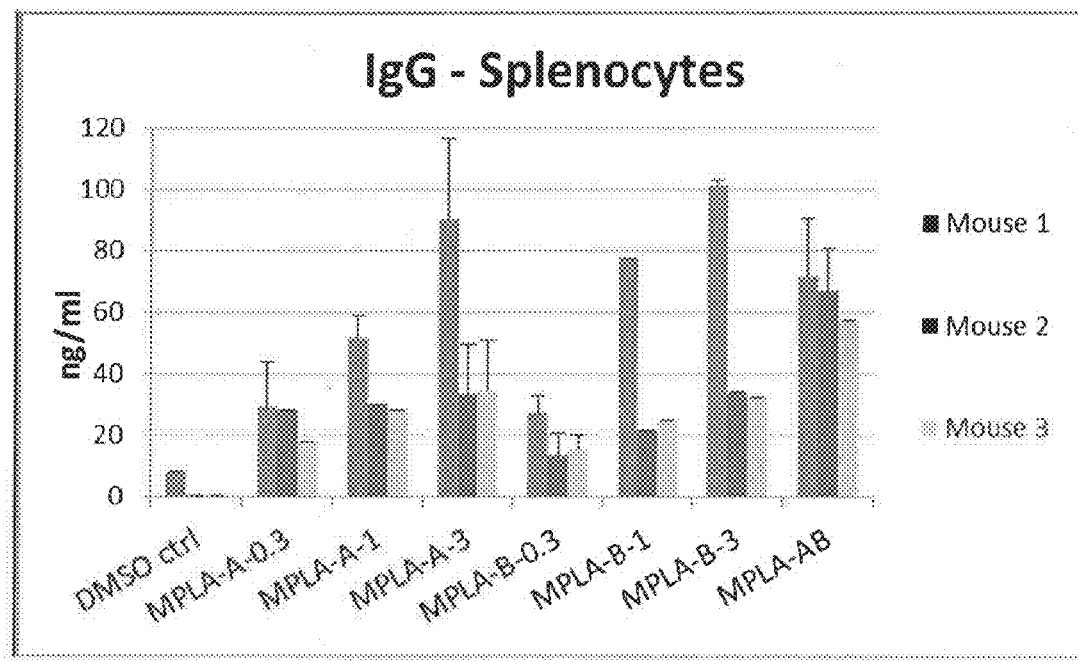
FIG. 4A shows the effect of the synthetic disaccharide lipid compounds of the present disclosure on IgG secretion from splenocytes in vitro.
Figure 4B:
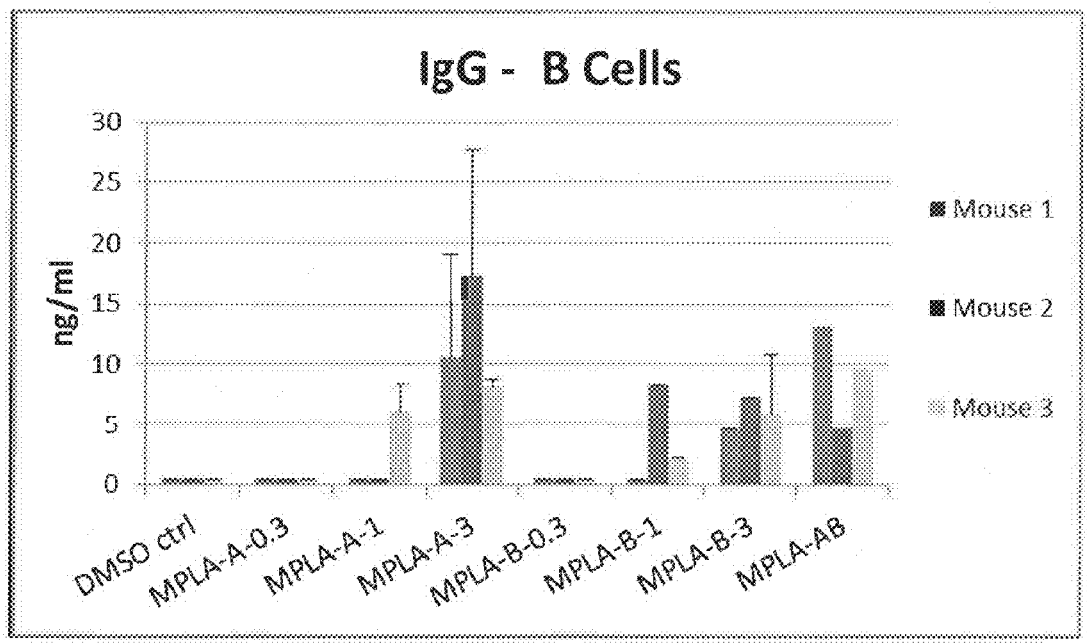
FIG. 4B shows the effect of the synthetic disaccharide lipid compounds of the present disclosure on IgG secretion from B cells in vitro.

Splenocytes and B cells were incubated with PHAD™ and MPLA-B, both alone and in combination, or solvent as a control to examine effects on the secretion of IgG. After 72 hours of incubation, supernatants were harvested for IgG determination. IgG levels, as quantitated by ELISA, are shown in FIGS. 4A and 4B for splenocytes and B cells, respectively. In splenocytes, PHAD™ and MPLA-B induced generally similar levels of IgG at all concentrations in mice 2 and 3, with the combination of PHAD™ and MPLA-B displaying the highest IgG levels, while IgG was induced in a dose-dependent manner in mouse 1 (FIG. 4A). In B cells, IgG was generally observed in all 3 mice at detectable levels only at the highest concentrations of PHAD™ and MPLA-B (3 µg/ml) (FIG. 4B).

Example 5

Synthetic Disaccharide Lipid Compounds Stimulate IL-12 Production In Vitro

In this example, the ability of the synthetic disaccharide lipid compounds of the present disclosure were tested for their ability to stimulate Interleukin (IL)-12 production from J774A cells (murine monocyte/macrophage cells derived a tumor in a female BALB/c mouse) in vitro. IL-12 is an important immune modulator as its expression during infection regulates innate responses and determines the type and duration of adaptive immune response. IL-12 induces interferon-γ (IFN-γ) production by natural killer cells, T cells, dendritic cells, and macrophages. IL-12 also promotes the differentiation of naive $CD4^+$ T cells into T helper 1 (Th1) cells that produce IFN-γ and aid in cell-mediated immunity. As IL-12 is induced by microbial products and regulates the development of adaptive immune cells, IL-12 plays a central role in coordinating innate and adaptive immunity. Therefore, IL-12 stimulation is a marker for immunostimulatory properties of a compound.

The synthetic disaccharide lipid compound used in this assay was that compound of the structure V (referred to herein as MPLA-B). As a comparison, results are also presented using the hexa-acyl disaccharide lipid compound known as PHAD™ (Avanti Polar Lipids, Alabaster, Ala.; also referred to herein as MPLA-A). PHAD™ has been shown to have immunostimulatory properties.

J774A cells were plated on 24 well plates at a density of $10^5$ cells/well and grown for 48 hours in DMEM with 10% FBS under standard cell culture conditions. Cells were serum-deprived for 18 h in media containing DMEM+0.5% FBS. PHAD and MPLA-B, dissolved in DMSO, were serially diluted and added to the serum-deprived cells (10 µL to 1 mL media) and incubated an additional 24 hours. Control wells received DMSO vehicle alone. The cell media containing IL-12 were harvested and centrifuged at 16,900×g for 10 minutes. The supernatants were transferred to fresh tubes and frozen at −80° C. until analysis. Mouse IL-12 (p40) was determined with a Mouse IL-12 p40 NonAllele-specific Quantikine ELISA (R&D Systems, Minneapolis, Minn.; catalogue No. MP 400).

Figure 5:
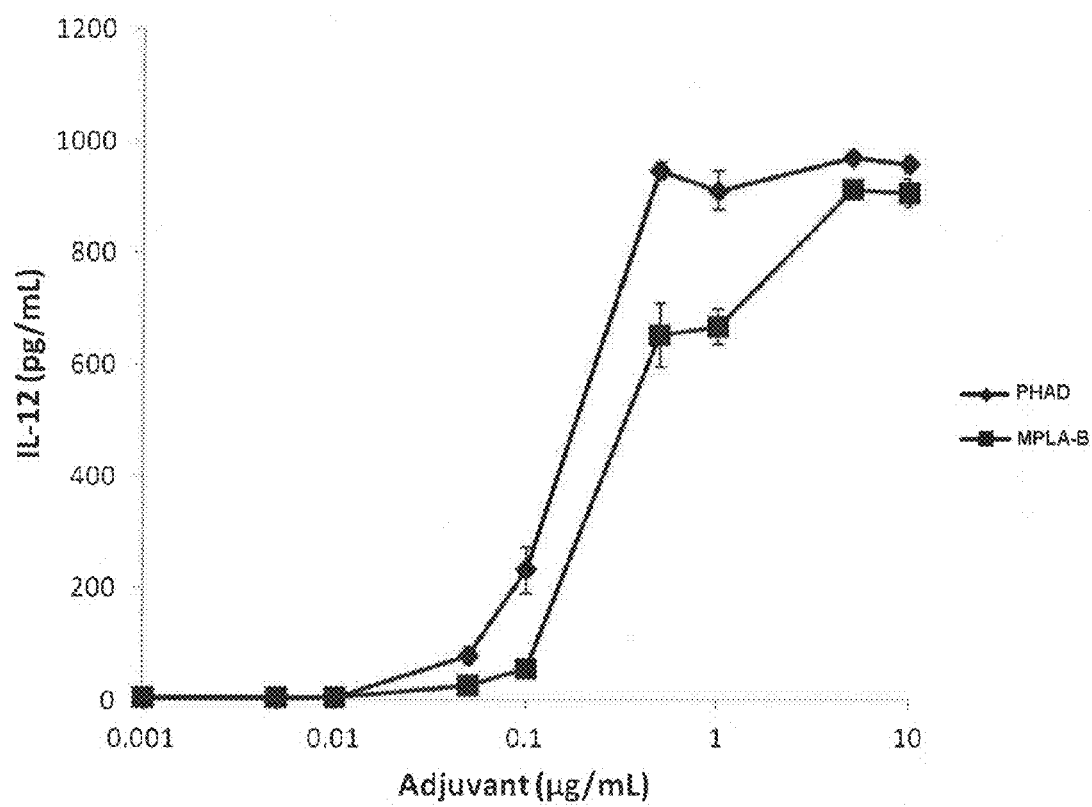
FIG. 5 shows the effect of the synthetic disaccharide lipid compounds of the present disclosure on IL-12 production from murine monocyte/macrophage cells in vitro.

The results are presented in FIG. 5. As can be seen, both MPLA-B and PHAD stimulated IL-12 production from J774A cells at similar concentrations, Maximum stimulation was seen in the 1-10 µg/ml range.

Example 6

Synthetic Disaccharide Lipid Compounds Stimulate an Immune Response In Vivo

In this example, the ability of the synthetic disaccharide lipid compounds of the present disclosure was tested for their ability to stimulate an immune response in vivo in a mouse model. Female C57BL/6 mice received a total of three 0.2 ml subcutaneous injections (at day 0, day 14 and day 28) of an exemplary synthetic disaccharide compound of the present disclosure (that compound shown having the general structure V, also referred to as MPLA-B or congener B), the hexa-acyl disaccharide lipid compound known as PHAD™ (Avanti Polar Lipids, Alabaster, Ala.; also referred to herein as MPLA-A) or a combination of the foregoing. PHAD™ has been shown to have immunostimulatory properties. A proprietary antigen (Pall-15) in combination with a proprietary liposomal vaccine formulation (AC Immune, Lausanne, Switzerland) was used in the vaccine preparation and for the induction of an amyloid-beta (Aβ)-specific antibody response. The vaccine preparation is described in PCT publication number WO2007/068411, titled Therapeutic Vaccine (which reference is hereby incorporated by reference for such teaching). On days 7, 21 and 35 post (three) injections, blood samples were collected and total Aβ-specific antibody response was determined by ELISA. Three difference vaccine dilutions were tested. The particulars of the vaccine administration protocol are as shown in Table 10. The indicated dilutions were made in phosphate buffered saline.

TABLE 10

| Group | Mice per group | Batch and volume[a] | Route of Administration[b] | Pall-15 (µg/dose)[c] | Quantity of PHAD (µg/dose)[c] | Quantity of MPLA-B (µg/dose)[c] |
|---|---|---|---|---|---|---|
| A | 5 | 0.2 ml (undiluted vaccine) | s.c. | 98.2 | 9.4 | — |
| B | 5 | 0.2 ml (undiluted vaccine) | s.c. | 91.6 | — | 12.4 |
| C | 5 | 0.2 ml (10x-diluted vaccine) | s.c. | 9.82 | 0.94 | — |
| D | 5 | 0.2 ml (10x-diluted vaccine) | s.c. | 9.16 | — | 1.24 |
| E | 5 | 0.2 ml (100x-diluted vaccine) | s.c. | 0.98 | 0/009 | — |
| F | 5 | 0.2 ml (100x-diluted vaccine) | s.c. | 0.92 | — | 0.012 |
| G | 5 | 0.2 ml (undiluted vaccine) Reference Batch | s.c. | 84 | 9.6 | 7 |

TABLE 10-continued

| Group | Mice per group | Batch and volume[a] | Route of Administration[b] | Pall-15 (µg/dose)[c] | Quantity of PHAD (µg/dose)[c] | Quantity of MPLA-B (µg/dose)[c] |
|---|---|---|---|---|---|---|
| H | 10 | 0.2 ml (undiluted vaccine) | s.c. | 94.6 | 5.6 | 4.8 |

Figure 6:
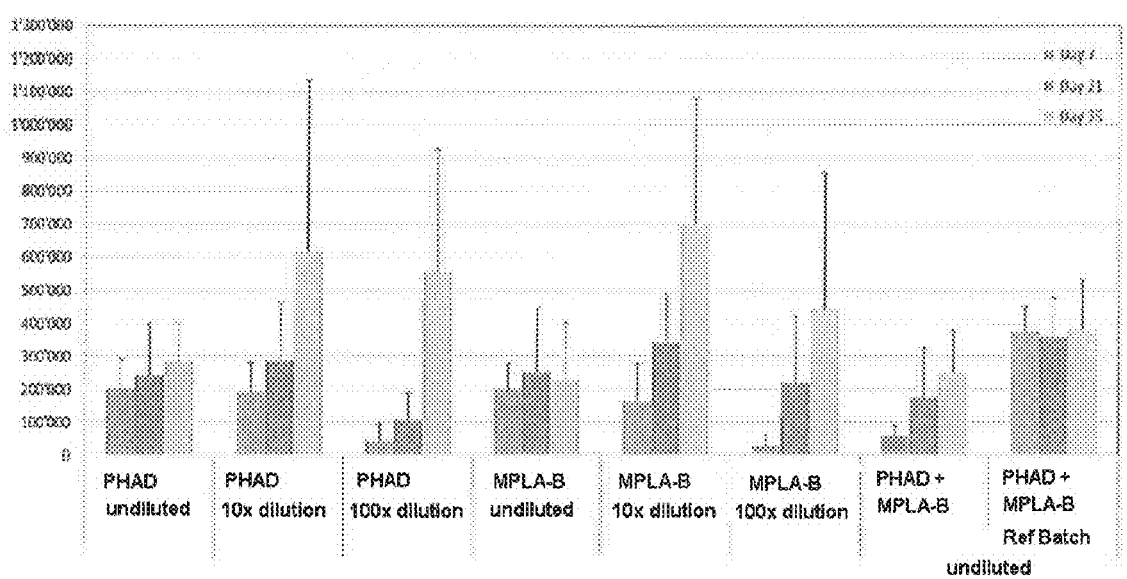
FIG. 6 shows the effect of the synthetic disaccharide lipid compounds of the present disclosure on stimulation of an antigen-specific immune response in vivo.

[a]Theoretical volume/dose
[b]Subcutaneous
[c]Measured quantity determined after analysis As shown in FIG. 6, all vaccine preparations induced a high anti-Aβ IgG antibody response similar to the reference batch (y axis shows concentration of antibody in ng/ml). There was no difference in the level of anti-Aβ IgG between the two vaccines prepared with the PHAD™ or MPLA-B at any time point (2-way ANOVA, Bonferroni posttest: P>0.05). Diluted vaccines were also tested (see Table 10). The level of anti-Aβ IgG remained elevated and similar to the undiluted vaccines. However, a boost effect was observed at day 35 (2-way ANOVA, Bonferroni posttest: P<0.0001) with a significant increase in antibody titers at day 35 for the vaccines with the 10× and 100× dilutions. At equal dose, no significant difference was found between the PHAD™ and MPLA-B, demonstrating equivalent immunogenicity of anti-Aβ vaccines. The combination of PHAD™ and MPLA-B was also effective. Results are expressed as mean±standard deviation obtained in groups of 5 and 10 mice.

What is claimed:

1. An essentially pure compound having the structure:

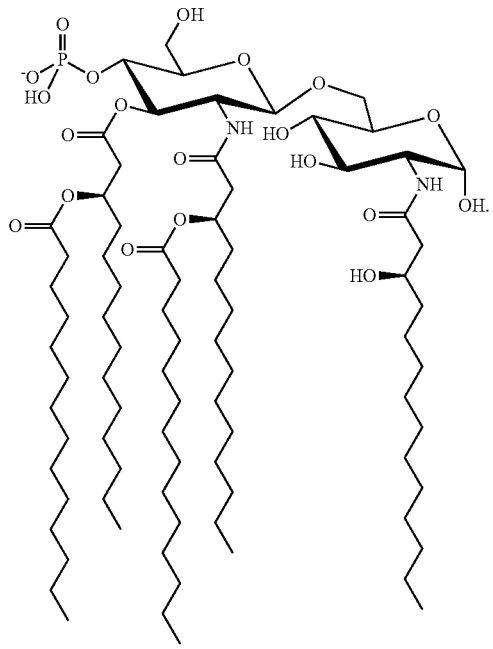

2. The essentially pure compound of claim 1, wherein the compounds is at least 95% pure with respect to the synthetic disaccharide lipid compounds as measured on a weight basis.

3. The essentially pure compound of claim 1, wherein the compounds is at least 99% pure with respect to the synthetic disaccharide lipid compounds as measured on a weight basis.

4. A pharmaceutical composition comprising:
   a. a pharmaceutically acceptable carrier;
   b. an optional antigen; and
   c. an essentially pure compound having the structure

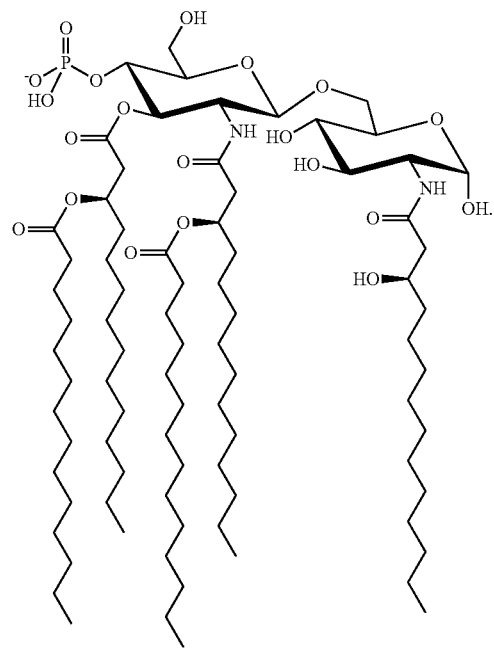

or a pharmaceutically acceptable salt thereof.

5. The pharmaceutical composition of claim 4, wherein the compounds is at least 95% pure with respect to the synthetic disaccharide lipid compounds as measured on a weight basis.

6. The pharmaceutical composition of claim 4, wherein the compounds is at least 99% pure with respect to the synthetic disaccharide lipid compounds as measured on a weight basis.

7. The pharmaceutical composition of claim 4, wherein the composition comprises an antigen.

8. The pharmaceutical composition of claim 4, wherein the composition further comprises a second adjuvant.

9. The pharmaceutical composition of claim 8, wherein the second adjuvant is a mono-phosphorylated hexaacyl disaccharide.

10. The pharmaceutical composition of claim 4, wherein the composition is a vaccine composition.

11. The pharmaceutical composition of claim 4, wherein the composition is useful in stimulating or enhancing an immune response in a subject.

12. The pharmaceutical composition of claim 4, wherein the pharmaceutically acceptable carrier is a liposome.

* * * * *